United States Patent
Johnson et al.

(10) Patent No.: US 10,196,656 B2
(45) Date of Patent: Feb. 5, 2019

(54) ENZYMES AND METHODS FOR DEALKYLATION OF SUBSTRATES

(71) Applicant: Alliance for Sustainable Energy, LLC, Golden, CO (US)

(72) Inventors: Christopher W. Johnson, Denver, CO (US); Gregg T. Beckham, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/065,717

(22) Filed: Mar. 9, 2016

(65) Prior Publication Data

US 2016/0265006 A1  Sep. 15, 2016

Related U.S. Application Data

(60) Provisional application No. 62/130,482, filed on Mar. 9, 2015.

(51) Int. Cl.
| | |
|---|---|
| *C12N 9/02* | (2006.01) |
| *C12N 9/04* | (2006.01) |
| *C12N 15/31* | (2006.01) |
| *C12N 15/53* | (2006.01) |
| *C12N 1/21* | (2006.01) |
| *C12P 7/22* | (2006.01) |

(52) U.S. Cl.
CPC .............. *C12P 7/22* (2013.01); *C12N 9/0071* (2013.01); *C12N 9/0095* (2013.01); *C12Y 114/00* (2013.01); *C12Y 118/01002* (2013.01)

(58) Field of Classification Search
None
See application file for complete search history.

(56) References Cited

U.S. PATENT DOCUMENTS 4,952,501 A  8/1990  Jasin et al.

OTHER PUBLICATIONS

Meunier et al., Chem. Rev. 104:3947-3980, 2004.*
Sang, H., Mechanisms of Development 121:1179-1186, 2004.*
GenBank Accession No. CP009110, Aug. 2014, first page only.*
Jeong et al., Genome Announc. 1:e00408-13, 2013, 2 pages.*
Guengerich, F. P., Nat. Rev. 1:359-366, 2002.*
Basch et al., J. Ind. Microbiol. Biotechnol. 34:171-176, 2007.*
Zong et al., Biotechnol. Appl. Biochem. 62:9-16, Jul. 2014.*
van Beilen et al., Appl. Environ. Microbiol. 71:1737-1744, 2005.*
Dictionary definition of "expression vector" from encyclopedia. com, last viewed on Aug. 17, 2017, 1 page.*
Lackie, J., "The Dictionary of Cell and Molecular Biology", Fourth Edition, 2007, p. 175.*
Girvan et al., Biochem. Soc. Trans. 34:1173-1177, 2006.*
Eun, H., "Enzymology Primer for Recombinant DNA Technology", Academic Press, Inc. San Diego, CA, p. 580.*
Hlavica, P., Biotechnol. Adv. 27:103-121, 2009.*
Tumen-Velasquez et al., "Accelerating pathway evolution by increasing the gene dosage of chromosomal segments", PNAS Jun. 2018, 6 pages, DOI:10.1073/pnas.1803745115 (Year: 2018).*
Gjermansen et al., "Proteins with GGDEF and EAL domains regulate Pseudomonas putida biofilm formation and dispersal", FEMS Microbiol. Lett. 265:215-224, 2006 (Year: 2006).*
Dardas et al., "The Demethylation of Guaiacol by a New Bacterial Cytochrome P-450", Archives of Biochemistry and Biophysics, Feb. 1985, vol. 236, No. 2, pp. 585-592.
Eltis et al., "Purification and characterization of cytochrome P45012121 from *Rhodococcus rhodochrous*", European Journal of Biochemistry / FEBS, 1993, vol. 213, No. 1, pp. 211-216.
Karlson et al., "Two Independently Regulated Cytochromes P-450 in a *Rhodoccus rhodochrous* Strain That Degrades 2-Ethoxyphenol and 4-Methoxybenzoate", Journal of Bacteriology, Mar. 1993, vol. 175, No. 5, pp. 1467-1474.
Kawahara et al., "Purification and Characterization of 2-ethoxyphenol-induced Cytochrome P450 from *Corynebacterium* sp. Strain EP1", Canadian Journal of Microbiology, 1999, vol. 45, No. 10, pp. 833-839.
Kim et al., "Physiological, Numerical and Molecular Characterization of alkyl ether-utilizing rhodococci", Environmental Microbiology, 2007, vol. 9, No. 6, pp. 1497-1510.
Nodate et al., "Functional Expression System for Cytochrome P450 Genes Using the Reductase Domain of Self-sufficient P450RhF from *Rhodococcus* sp. NCIMB 9784", Applied Genetics and Molecular Biotechnology, 2006, vol. 71, No. 4, pp. 455-462.
Patrauchan et al., "Catabolism of Benzoate and Phthalate in *Rhodococcus* sp. Strain RHA1: Redundancies and Convergence", Journal of Bacteriolgy, Jun. 2005, vol. 187, No. 12, pp. 4050-4063.
Sauret-Ignazi et al., "Purification and Properties of Cytochrome P-450 from *Moraxella* sp.", Biochimie, Oct. 1988, vol. 70, No. 10, pp. 1385-1395.
S terjiades et al., "Properties of a Bacterial Strain Able to Grow on Guaiacol", FEMS Microbiology Letters, May 1982, vol. 14, No. 1, pp. 57-60.
S tudenik et al., "Characterization of an O-Demethylase of *Desulfitobacterium hafniense* DCB-2", Journal of Bacteriology, 2012, vol. 194, No. 13, pp. 3317-3326.
Sutherland, "Demethylation of Veratrole by Cytochrome P-450 in *Streptomyces setonii*", Applied and Environmental Microbiology, Jul. 1986, vol. 52, No. 1, pp. 98-100.

* cited by examiner

*Primary Examiner* — David Steadman
(74) *Attorney, Agent, or Firm* — John C. Stolpa; Alexandra M. Hall

(57) ABSTRACT

Disclosed herein are enzymes and organisms useful for the dealkylation of products derived from lignin depolymerization, including the conversion of guaiacol or guaethol to catechol or the conversion of anisole to phenol. Methods of converting guaiacol or guaethol to catechol or anisole to phenol using enzymes or organisms expressing the same are also disclosed.

7 Claims, 9 Drawing Sheets

Specification includes a Sequence Listing.

Figure 2

FIG. 2A. (SEQ ID NO:1)

```
ATGACGACGACCGAACGGCCCGATCTCGCCTGGCTCGACGAGGTCACCATGACGCAGCTCGA
GCGCAACCCGTACGAGGTGTACGAGCGGCTGCGCGCGGAGGCGCCGCTGGCCTTCGTGCCGG
TGCTGGGGTCCTACGTCGCCTCGACCGCCGAGGTCTGCCGCGAAGTCGCGACCAGCCCGGAC
TTCGAGGCCGTCATCACCCCGGCCGGCGGCCGCACCTTCGGGCACCCGGCGATCATCGGCGT
CAACGGCGACATCCACGCCGACCTGCGCTCCATGGTCGAGCCCGCCCTGCAGCCCGCCGAGG
TGGACCGCTGGATCGACGACCTGGTGCGGCCCATCGCGCGCCGCTACCTGGAGCGGTTCGAA
AACGACGGGCACGCCGAACTGGTGGCGCAGTACTGCGAGCCGGTCAGCGTCCGCTCGCTCGG
CGACCTGCTCGGCCTGCAGGAGGTCGACTCGGACAAGCTGCGCGAGTGGTTCGCCAAGCTGA
ACCGCTCGTTCACCAACGCCGCCGTCGACGAGAACGGCGAGTTCGCCAACCCCGAGGGCTTC
GCCGAGGGCGACCAGGCGAAGGCCGAGATCCGCGCCGTCGTCGACCCGCTGATCGACAAGTG
GATCGAGCACCCCGACGACAGCGCCATTTCGCACTGGCTGCACGACGGCATGCCGCCCGGCC
AGACCCGCGACCGCGAGTACATCTACCCGACGATCTACGTGTACCTGCTCGGCGCGATGCAG
GAACCCGGCCACGGCATGGCCTCCACCCTGGTCGGCCTGTTCAGCAGGCCCGAGCAGCTGGA
AGAGGTGGTCGACGACCCCACGCTGATCCCGCGGGCGATCGCCGAGGGCCTGCGGTGGACCT
CGCCGATCTGGTCGGCCACCGCCCGCATCTCCACCAAGCCGGTGACCATCGCCGGGGTCGAC
CTGCCCGCCGGCACGCCGGTGATGCTCTCCTACGGCTCGGCCAACCACGACACCGGCAAGTA
CGAGGCGCCCTCGCAGTACGACCTGCACGCCCGCCGCTGCCGCACCTCGCCTTCGGCGCGG
GCAACCACGCGTGCGCGGGCATCTACTTCGCCAACCACGTCATGCGGATCGCGCTGGAGGAG
CTGTTCGAGGCCATCCCGAACCTGGAGCGCGACACCCGCGAGGGCGTCGAGTTCTGGGGCTG
GGGCTTCCGCGGCCCCACCTCGCTGCACGTCACCTGGGAGGTG
```

FIG. 2B. (SEQ ID NO:2)

FIG. 3A.   (SEQ ID NO:3)

GTGACGTTCGCGGTCAGCGTCGGGGGCAGGCGGGTCGACTGCGAGCCCGGCCAGACCCTGCT
CGAGGCGTTCCTGCGCGGCGGGGTGTGGATGCCCAACTCGTGCAACCAGGGCACCTGCGGCA
CCTGCAAGCTCCAGGTGCTCTCCGGCGAGGTCGACCACGGCGGCGCCCCGGAGGACACCCTC
AGCGCCGAGGAACGCGCGTCCGGACTGGCGCTCGCCTGCCAGGCCCGTCCGCTCGCCGACAC
GGAGGTGCGCAGCACCGCCGACGCCGGGCGCGTCACGCACCCGCTGCGGGACCTGACGGCCA
CCGTGCTGGAGGTCGCCGACATCGCGCGCGACACCCGCCGGGTGCTGCTGGGCCTGGCCGAG
CCGCTGGCGTTCGAGGCCGGGCAGTACGTCGAGCTGGTCGTGCCCGGCTCCGGCGCGCGGCG
GCAGTACTCGCTGGCCAACACGGCCGACGAGGACAAGGTGCTGGAGCTGCACGTCCGGCGCG
TGCCCGGTGGGGTCGCCACCGACGGCTGGCTCTTCGACGGGCTCGCCGCCGGCGACCGGGTC
GAGGCGACCGGGCCGCTCGGCGACTTCCACCTGCCGCCGCCGGACGAGGACGACGGCGGCCC
GATGGTGCTCATCGGCGGCGGAACCGGGCTGGCGCCGCTGGTCGGCATCGCCCGCACCGCGC
TGGCCCGGCACCCGTCGCGCGAAGTGCTGCTGTACCACGGGGTGCGCGGCGCGGCGGACCTG
TACGACCTCGGCCGGTTCGCCGAGATCGCGGAGGAGCACCCGGGTTTCCGGTTCGTGCCGGT
GCTGTCGGACGAGCCGGATCCGGCGTACCGGGGCGGTTTCCCGACCGACGCGTTCGTCGAGG
ACGTCCCCAGTGGACGCGGCTGGTCCGGCTGGCTGTGCGGCCCGCCGGCGATGGTCGAGGCC
GGGGTGAAGGCGTTCAAACGGCGGCGCATGTCGCCGCGGCGGATCCACCGGGAGAAGTTCAC
GCCGGCCTCG

FIG. 3B.   (SEQ ID NO:4)

M T F A V S V G G R R V D C E P G Q T L L E A F L R G G V W M
P N S C N Q G T C G T C K L Q V L S G E V D H G G A P E D T L
S A E E R A S G L A L A C Q A R P L A D T E V R S T A D A G R
V T H P L R D L T A T V L E V A D I A R D T R R V L L G L A E
P L A F E A G Q Y V E L V V P G S G A R R Q Y S L A N T A D E
D K V L E L H V R R V P G G V A T D G W L F D G L A A G D R V
E A T G P L G D F H L P P P D E D D G G P M V L I G G G T G L
A P L V G I A R T A L A R H P S R E V L L Y H G V R G A A D L
Y D L G R F A E I A E E H P G F R F V P V L S D E P D P A Y R
G G F P T D A F V E D V P S G R G W S G W L C G P P A M V E A
G V K A F K R R R M S P R R I H R E K F T P A S

SEQUENCE LISTING

```
<160> NUMBER OF SEQ ID NOS: 17

<210> SEQ ID NO 1
<211> LENGTH: 1221
<212> TYPE: DNA
<213> ORGANISM: Amycolatopsis sp. ATCC 39116
<220> FEATURE:
<221> NAME/KEY: CDS
<222> LOCATION: (1)..(1221)

<400> SEQUENCE: 1 atg acg acg acc gaa cgg ccc gat ctc gcc tgg ctc gac gag gtc acc      48
Met Thr Thr Thr Glu Arg Pro Asp Leu Ala Trp Leu Asp Glu Val Thr
1               5                  10                  15 atg acg cag ctc gag cgc aac ccg tac gag gtg tac gag cgg ctg cgc      96
Met Thr Gln Leu Glu Arg Asn Pro Tyr Glu Val Tyr Glu Arg Leu Arg
            20                  25                  30 gcg gag gcg ccg ctg gcc ttc gtg ccg gtg ctg ggg tcc tac gtc gcc     144
Ala Glu Ala Pro Leu Ala Phe Val Pro Val Leu Gly Ser Tyr Val Ala
        35                  40                  45 tcg acc gcc gag gtc tgc cgc gaa gtc gcg acc agc ccg gac ttc gag     192
Ser Thr Ala Glu Val Cys Arg Glu Val Ala Thr Ser Pro Asp Phe Glu
    50                  55                  60 gcc gtc atc acc ccg gcc ggc ggc cgc acc ttc ggg cac ccg gcg atc     240
Ala Val Ile Thr Pro Ala Gly Gly Arg Thr Phe Gly His Pro Ala Ile
65                  70                  75                  80 atc ggc gtc aac ggc gac atc cac gcc gac ctg cgc tcc atg gtc gag     288
Ile Gly Val Asn Gly Asp Ile His Ala Asp Leu Arg Ser Met Val Glu
                85                  90                  95 ccc gcc ctg cag ccc gcc gag gtg gac cgc tgg atc gac gac ctg gtg     336
Pro Ala Leu Gln Pro Ala Glu Val Asp Arg Trp Ile Asp Asp Leu Val
            100                 105                 110 cgg ccc atc gcg cgc cgc tac ctg gag cgg ttc gaa aac gac ggg cac     384
Arg Pro Ile Ala Arg Arg Tyr Leu Glu Arg Phe Glu Asn Asp Gly His
        115                 120                 125 gcc gaa ctg gtg gcg cag tac tgc gag ccg gtc agc gtc cgc tcg ctc     432
Ala Glu Leu Val Ala Gln Tyr Cys Glu Pro Val Ser Val Arg Ser Leu
    130                 135                 140 ggc gac ctg ctc ggc ctg cag gag gtc gac tcg gac aag ctg cgc gag     480
Gly Asp Leu Leu Gly Leu Gln Glu Val Asp Ser Asp Lys Leu Arg Glu
145                 150                 155                 160
```

| | | |
|---|---|---|
| tgg ttc gcc aag ctg aac cgc tcg ttc acc aac gcc gcc gtc gac gag<br>Trp Phe Ala Lys Leu Asn Arg Ser Phe Thr Asn Ala Ala Val Asp Glu<br>165 170 175 | | 528 |
| aac ggc gag ttc gcc aac ccc gag ggc ttc gcc gag ggc gac cag gcg<br>Asn Gly Glu Phe Ala Asn Pro Glu Gly Phe Ala Glu Gly Asp Gln Ala<br>180 185 190 | | 576 |
| aag gcc gag atc cgc gcc gtc gtc gac ccg ctg atc gac aag tgg atc<br>Lys Ala Glu Ile Arg Ala Val Val Asp Pro Leu Ile Asp Lys Trp Ile<br>195 200 205 | | 624 |
| gag cac ccc gac gac agc gcc att tcg cac tgg ctg cac gac ggc atg<br>Glu His Pro Asp Asp Ser Ala Ile Ser His Trp Leu His Asp Gly Met<br>210 215 220 | | 672 |
| ccg ccc ggc cag acc cgc gac cgc gag tac atc tac ccg acg atc tac<br>Pro Pro Gly Gln Thr Arg Asp Arg Glu Tyr Ile Tyr Pro Thr Ile Tyr<br>225 230 235 240 | | 720 |
| gtg tac ctg ctc ggc gcg atg cag gaa ccc ggc cac ggc atg gcc tcc<br>Val Tyr Leu Leu Gly Ala Met Gln Glu Pro Gly His Gly Met Ala Ser<br>245 250 255 | | 768 |
| acc ctg gtc ggc ctg ttc agc agg ccc gag cag ctg gaa gag gtg gtc<br>Thr Leu Val Gly Leu Phe Ser Arg Pro Glu Gln Leu Glu Glu Val Val<br>260 265 270 | | 816 |
| gac gac ccc acg ctg atc ccg cgg gcg atc gcc gag ggc ctg cgg tgg<br>Asp Asp Pro Thr Leu Ile Pro Arg Ala Ile Ala Glu Gly Leu Arg Trp<br>275 280 285 | | 864 |
| acc tcg ccg atc tgg tcg gcc acc gcc cgc atc tcc acc aag ccg gtg<br>Thr Ser Pro Ile Trp Ser Ala Thr Ala Arg Ile Ser Thr Lys Pro Val<br>290 295 300 | | 912 |
| acc atc gcc ggg gtc gac ctg ccc gcc ggc acg ccg gtg atg ctc tcc<br>Thr Ile Ala Gly Val Asp Leu Pro Ala Gly Thr Pro Val Met Leu Ser<br>305 310 315 320 | | 960 |
| tac ggc tcg gcc aac cac gac acc ggc aag tac gag gcg ccc tcg cag<br>Tyr Gly Ser Ala Asn His Asp Thr Gly Lys Tyr Glu Ala Pro Ser Gln<br>325 330 335 | | 1008 |
| tac gac ctg cac cgc ccg ccg ctg ccg cac ctc gcc ttc ggc gcg ggc<br>Tyr Asp Leu His Arg Pro Pro Leu Pro His Leu Ala Phe Gly Ala Gly<br>340 345 350 | | 1056 |
| aac cac gcg tgc gcg ggc atc tac ttc gcc aac cac gtc atg cgg atc<br>Asn His Ala Cys Ala Gly Ile Tyr Phe Ala Asn His Val Met Arg Ile<br>355 360 365 | | 1104 |
| gcg ctg gag gag ctg ttc gag gcc atc ccg aac ctg gag cgc gac acc<br>Ala Leu Glu Glu Leu Phe Glu Ala Ile Pro Asn Leu Glu Arg Asp Thr<br>370 375 380 | | 1152 |
| cgc gag ggc gtc gag ttc tgg ggc tgg ggc ttc cgc ggc ccc acc tcg<br>Arg Glu Gly Val Glu Phe Trp Gly Trp Gly Phe Arg Gly Pro Thr Ser<br>385 390 395 400 | | 1200 |
| ctg cac gtc acc tgg gag gtg<br>Leu His Val Thr Trp Glu Val<br>405 | | 1221 |

<210> SEQ ID NO 2
<211> LENGTH: 407
<212> TYPE: PRT
<213> ORGANISM: Amycolatopsis sp. ATCC 39116

<400> SEQUENCE: 2

Met Thr Thr Thr Glu Arg Pro Asp Leu Ala Trp Leu Asp Glu Val Thr
1               5                   10                  15

Met Thr Gln Leu Glu Arg Asn Pro Tyr Glu Val Tyr Glu Arg Leu Arg
            20                  25                  30

Ala Glu Ala Pro Leu Ala Phe Val Pro Val Leu Gly Ser Tyr Val Ala

```
            35                  40                  45
Ser Thr Ala Glu Val Cys Arg Glu Val Ala Thr Ser Pro Asp Phe Glu
 50                  55                  60

Ala Val Ile Thr Pro Ala Gly Gly Arg Thr Phe Gly His Pro Ala Ile
 65                  70                  75                  80

Ile Gly Val Asn Gly Asp Ile His Ala Asp Leu Arg Ser Met Val Glu
                 85                  90                  95

Pro Ala Leu Gln Pro Ala Glu Val Asp Arg Trp Ile Asp Asp Leu Val
                100                 105                 110

Arg Pro Ile Ala Arg Arg Tyr Leu Glu Arg Phe Glu Asn Asp Gly His
            115                 120                 125

Ala Glu Leu Val Ala Gln Tyr Cys Glu Pro Val Ser Val Arg Ser Leu
        130                 135                 140

Gly Asp Leu Leu Gly Leu Gln Glu Val Asp Ser Asp Lys Leu Arg Glu
145                 150                 155                 160

Trp Phe Ala Lys Leu Asn Arg Ser Phe Thr Asn Ala Ala Val Asp Glu
                165                 170                 175

Asn Gly Glu Phe Ala Asn Pro Glu Gly Phe Ala Glu Gly Asp Gln Ala
                180                 185                 190

Lys Ala Glu Ile Arg Ala Val Val Asp Pro Leu Ile Asp Lys Trp Ile
            195                 200                 205

Glu His Pro Asp Asp Ser Ala Ile Ser His Trp Leu His Asp Gly Met
        210                 215                 220

Pro Pro Gly Gln Thr Arg Asp Arg Glu Tyr Ile Tyr Pro Thr Ile Tyr
225                 230                 235                 240

Val Tyr Leu Leu Gly Ala Met Gln Glu Pro Gly His Gly Met Ala Ser
                245                 250                 255

Thr Leu Val Gly Leu Phe Ser Arg Pro Glu Gln Leu Glu Glu Val Val
                260                 265                 270

Asp Asp Pro Thr Leu Ile Pro Arg Ala Ile Ala Glu Gly Leu Arg Trp
            275                 280                 285

Thr Ser Pro Ile Trp Ser Ala Thr Ala Arg Ile Ser Thr Lys Pro Val
        290                 295                 300

Thr Ile Ala Gly Val Asp Leu Pro Ala Gly Thr Pro Val Met Leu Ser
305                 310                 315                 320

Tyr Gly Ser Ala Asn His Asp Thr Gly Lys Tyr Glu Ala Pro Ser Gln
                325                 330                 335

Tyr Asp Leu His Arg Pro Pro Leu Pro His Leu Ala Phe Gly Ala Gly
            340                 345                 350

Asn His Ala Cys Ala Gly Ile Tyr Phe Ala Asn His Val Met Arg Ile
        355                 360                 365

Ala Leu Glu Glu Leu Phe Glu Ala Ile Pro Asn Leu Glu Arg Asp Thr
    370                 375                 380

Arg Glu Gly Val Glu Phe Trp Gly Trp Gly Phe Arg Gly Pro Thr Ser
385                 390                 395                 400

Leu His Val Thr Trp Glu Val
                405

<210> SEQ ID NO 3
<211> LENGTH: 1002
<212> TYPE: DNA
<213> ORGANISM: Amycolatopsis sp. ATCC 39116
<220> FEATURE:
<221> NAME/KEY: CDS
<222> LOCATION: (1)..(1002)
```

<400> SEQUENCE: 3

| | | | | | | | | | | | | | | | | |
|---|---|---|---|---|---|---|---|---|---|---|---|---|---|---|---|---|
| gtg | acg | ttc | gcg | gtc | agc | gtc | ggg | ggc | agg | cgg | gtc | gac | tgc | gag | ccc | 48 |
| Met | Thr | Phe | Ala | Val | Ser | Val | Gly | Gly | Arg | Arg | Val | Asp | Cys | Glu | Pro | |
| 1 | | | | 5 | | | | | 10 | | | | | 15 | | |
| ggc | cag | acc | ctg | ctc | gag | gcg | ttc | ctg | cgc | ggc | ggg | gtg | tgg | atg | ccc | 96 |
| Gly | Gln | Thr | Leu | Leu | Glu | Ala | Phe | Leu | Arg | Gly | Gly | Val | Trp | Met | Pro | |
| | | 20 | | | | | 25 | | | | | 30 | | | | |
| aac | tcg | tgc | aac | cag | ggc | acc | tgc | ggc | acc | tgc | aag | ctc | cag | gtg | ctc | 144 |
| Asn | Ser | Cys | Asn | Gln | Gly | Thr | Cys | Gly | Thr | Cys | Lys | Leu | Gln | Val | Leu | |
| | | | 35 | | | | | 40 | | | | | 45 | | | |
| tcc | ggc | gag | gtc | gac | cac | ggc | ggc | gcc | ccg | gag | gac | acc | ctc | agc | gcc | 192 |
| Ser | Gly | Glu | Val | Asp | His | Gly | Gly | Ala | Pro | Glu | Asp | Thr | Leu | Ser | Ala | |
| 50 | | | | | 55 | | | | | 60 | | | | | | |
| gag | gaa | cgc | gcg | tcc | gga | ctg | gcg | ctc | gcc | tgc | cag | gcc | cgt | ccg | ctc | 240 |
| Glu | Glu | Arg | Ala | Ser | Gly | Leu | Ala | Leu | Ala | Cys | Gln | Ala | Arg | Pro | Leu | |
| 65 | | | | | 70 | | | | | 75 | | | | | 80 | |
| gcc | gac | acg | gag | gtg | cgc | agc | acc | gcc | gac | gcc | ggg | cgc | gtc | acg | cac | 288 |
| Ala | Asp | Thr | Glu | Val | Arg | Ser | Thr | Ala | Asp | Ala | Gly | Arg | Val | Thr | His | |
| | | | | 85 | | | | | 90 | | | | | 95 | | |
| ccg | ctg | cgg | gac | ctg | acg | gcc | acc | gtg | ctg | gag | gtc | gcc | gac | atc | gcg | 336 |
| Pro | Leu | Arg | Asp | Leu | Thr | Ala | Thr | Val | Leu | Glu | Val | Ala | Asp | Ile | Ala | |
| | | | 100 | | | | | 105 | | | | | 110 | | | |
| cgc | gac | acc | cgc | cgg | gtg | ctg | ctg | ggc | ctg | gcc | gag | ccg | ctg | gcg | ttc | 384 |
| Arg | Asp | Thr | Arg | Arg | Val | Leu | Leu | Gly | Leu | Ala | Glu | Pro | Leu | Ala | Phe | |
| | | | | 115 | | | | | 120 | | | | | 125 | | |
| gag | gcc | ggg | cag | tac | gtc | gag | ctg | gtc | gtg | ccc | ggc | tcc | ggc | gcg | cgg | 432 |
| Glu | Ala | Gly | Gln | Tyr | Val | Glu | Leu | Val | Val | Pro | Gly | Ser | Gly | Ala | Arg | |
| | | 130 | | | | | 135 | | | | | 140 | | | | |
| cgg | cag | tac | tcg | ctg | gcc | aac | acg | gcc | gac | gag | gac | aag | gtg | ctg | gag | 480 |
| Arg | Gln | Tyr | Ser | Leu | Ala | Asn | Thr | Ala | Asp | Glu | Asp | Lys | Val | Leu | Glu | |
| 145 | | | | | 150 | | | | | 155 | | | | | 160 | |
| ctg | cac | gtc | cgg | cgc | gtg | ccc | ggt | ggg | gtc | gcc | acc | gac | ggc | tgg | ctc | 528 |
| Leu | His | Val | Arg | Arg | Val | Pro | Gly | Gly | Val | Ala | Thr | Asp | Gly | Trp | Leu | |
| | | | | 165 | | | | | 170 | | | | | 175 | | |
| ttc | gac | ggg | ctc | gcc | gcc | ggc | gac | cgg | gtc | gag | gcg | acc | ggg | ccg | ctc | 576 |
| Phe | Asp | Gly | Leu | Ala | Ala | Gly | Asp | Arg | Val | Glu | Ala | Thr | Gly | Pro | Leu | |
| | | | 180 | | | | | 185 | | | | | 190 | | | |
| ggc | gac | ttc | cac | ctg | ccg | ccg | ccg | gac | gag | gac | gac | ggc | ggc | ccg | atg | 624 |
| Gly | Asp | Phe | His | Leu | Pro | Pro | Pro | Asp | Glu | Asp | Asp | Gly | Gly | Pro | Met | |
| | | | | 195 | | | | | 200 | | | | | 205 | | |
| gtg | ctc | atc | ggc | ggc | gga | acc | ggg | ctg | gcg | ccg | ctg | gtc | ggc | atc | gcc | 672 |
| Val | Leu | Ile | Gly | Gly | Gly | Thr | Gly | Leu | Ala | Pro | Leu | Val | Gly | Ile | Ala | |
| | | 210 | | | | | 215 | | | | | 220 | | | | |
| cgc | acc | gcg | ctg | gcc | cgg | cac | ccg | tcg | cgc | gaa | gtg | ctg | ctg | tac | cac | 720 |
| Arg | Thr | Ala | Leu | Ala | Arg | His | Pro | Ser | Arg | Glu | Val | Leu | Leu | Tyr | His | |
| 225 | | | | | 230 | | | | | 235 | | | | | 240 | |
| ggg | gtg | cgc | ggc | gcg | gcg | gac | ctg | tac | gac | ctc | ggc | cgg | ttc | gcc | gag | 768 |
| Gly | Val | Arg | Gly | Ala | Ala | Asp | Leu | Tyr | Asp | Leu | Gly | Arg | Phe | Ala | Glu | |
| | | | | 245 | | | | | 250 | | | | | 255 | | |
| atc | gcg | gag | gag | cac | ccg | ggt | ttc | cgg | ttc | gtg | ccg | gtg | ctg | tcg | gac | 816 |
| Ile | Ala | Glu | Glu | His | Pro | Gly | Phe | Arg | Phe | Val | Pro | Val | Leu | Ser | Asp | |
| | | | 260 | | | | | 265 | | | | | 270 | | | |
| gag | ccg | gat | ccg | gcg | tac | cgg | ggc | ggt | ttc | ccg | acc | gac | gcg | ttc | gtc | 864 |
| Glu | Pro | Asp | Pro | Ala | Tyr | Arg | Gly | Gly | Phe | Pro | Thr | Asp | Ala | Phe | Val | |
| | | | | 275 | | | | | 280 | | | | | 285 | | |
| gag | gac | gtc | ccc | agt | gga | cgc | ggc | tgg | tcc | ggc | tgg | ctg | tgc | ggc | ccg | 912 |
| Glu | Asp | Val | Pro | Ser | Gly | Arg | Gly | Trp | Ser | Gly | Trp | Leu | Cys | Gly | Pro | |
| | | 290 | | | | | 295 | | | | | 300 | | | | |

```
ccg gcg atg gtc gag gcc ggg gtg aag gcg ttc aaa cgg cgg cgc atg    960
Pro Ala Met Val Glu Ala Gly Val Lys Ala Phe Lys Arg Arg Arg Met
305                 310                 315                 320 tcg ccg cgg cgg atc cac cgg gag aag ttc acg ccg gcc tcg            1002
Ser Pro Arg Arg Ile His Arg Glu Lys Phe Thr Pro Ala Ser
                325                 330
```

<210> SEQ ID NO 4
<211> LENGTH: 334
<212> TYPE: PRT
<213> ORGANISM: Amycolatopsis sp. ATCC 39116

<400> SEQUENCE: 4

```
Met Thr Phe Ala Val Ser Val Gly Gly Arg Arg Val Asp Cys Glu Pro
1               5                   10                  15

Gly Gln Thr Leu Leu Glu Ala Phe Leu Arg Gly Gly Val Trp Met Pro
            20                  25                  30

Asn Ser Cys Asn Gln Gly Thr Cys Gly Thr Cys Lys Leu Gln Val Leu
        35                  40                  45

Ser Gly Glu Val Asp His Gly Gly Ala Pro Glu Asp Thr Leu Ser Ala
    50                  55                  60

Glu Glu Arg Ala Ser Gly Leu Ala Leu Ala Cys Gln Ala Arg Pro Leu
65                  70                  75                  80

Ala Asp Thr Glu Val Arg Ser Thr Ala Asp Ala Gly Arg Val Thr His
                85                  90                  95

Pro Leu Arg Asp Leu Thr Ala Thr Val Leu Glu Val Ala Asp Ile Ala
            100                 105                 110

Arg Asp Thr Arg Arg Val Leu Leu Gly Leu Ala Glu Pro Leu Ala Phe
        115                 120                 125

Glu Ala Gly Gln Tyr Val Glu Leu Val Val Pro Gly Ser Gly Ala Arg
    130                 135                 140

Arg Gln Tyr Ser Leu Ala Asn Thr Ala Asp Glu Asp Lys Val Leu Glu
145                 150                 155                 160

Leu His Val Arg Arg Val Pro Gly Gly Val Ala Thr Asp Gly Trp Leu
                165                 170                 175

Phe Asp Gly Leu Ala Ala Gly Asp Arg Val Glu Ala Thr Gly Pro Leu
            180                 185                 190

Gly Asp Phe His Leu Pro Pro Asp Glu Asp Gly Gly Pro Met
        195                 200                 205

Val Leu Ile Gly Gly Gly Thr Gly Leu Ala Pro Leu Val Gly Ile Ala
    210                 215                 220

Arg Thr Ala Leu Ala Arg His Pro Ser Arg Glu Val Leu Leu Tyr His
225                 230                 235                 240

Gly Val Arg Gly Ala Ala Asp Leu Tyr Asp Leu Gly Arg Phe Ala Glu
                245                 250                 255

Ile Ala Glu Glu His Pro Gly Phe Arg Phe Val Pro Val Leu Ser Asp
            260                 265                 270

Glu Pro Asp Pro Ala Tyr Arg Gly Gly Phe Pro Thr Asp Ala Phe Val
        275                 280                 285

Glu Asp Val Pro Ser Gly Arg Gly Trp Ser Gly Trp Leu Cys Gly Pro
    290                 295                 300

Pro Ala Met Val Glu Ala Gly Val Lys Ala Phe Lys Arg Arg Arg Met
305                 310                 315                 320

Ser Pro Arg Arg Ile His Arg Glu Lys Phe Thr Pro Ala Ser
                325                 330
```

```
<210> SEQ ID NO 5
<211> LENGTH: 1209
<212> TYPE: DNA
<213> ORGANISM: Rhodococcus pyridinivorans AK37
<220> FEATURE:
<221> NAME/KEY: CDS
<222> LOCATION: (1)..(1209)

<400> SEQUENCE: 5 atg acc agc acc ctt tcg tgg ctc gac gag atc acc atg gaa gaa ctc        48
Met Thr Ser Thr Leu Ser Trp Leu Asp Glu Ile Thr Met Glu Glu Leu
1               5                   10                  15 gag cgc aat ccg tac ccg gtc tac gag cgc ttg cgt gcc gaa gct ccg        96
Glu Arg Asn Pro Tyr Pro Val Tyr Glu Arg Leu Arg Ala Glu Ala Pro
            20                  25                  30 gtc gcc ttc gtg ccc gtc ctc ggc gcc tac gta gcg tcc acg acc gaa       144
Val Ala Phe Val Pro Val Leu Gly Ala Tyr Val Ala Ser Thr Thr Glu
        35                  40                  45 gcg tgc cgt gcg gtc gcg gcc ggc gac gac ttc gac ggc atc atc acc       192
Ala Cys Arg Ala Val Ala Ala Gly Asp Asp Phe Asp Gly Ile Ile Thr
    50                  55                  60 ccc gcc ggt ggc cgc acc ttc ggt cat ccc gcg atc atc ggc gtc aac       240
Pro Ala Gly Gly Arg Thr Phe Gly His Pro Ala Ile Ile Gly Val Asn
65                  70                  75                  80 ggc gac atc cac cgc gac ctg cgg tcg atg gtc gaa ccc gcc ctc cag       288
Gly Asp Ile His Arg Asp Leu Arg Ser Met Val Glu Pro Ala Leu Gln
                85                  90                  95 ccc gcc gag gtg gac cgc tgg atc gag gat ctc gtc cgc ccg atc gca       336
Pro Ala Glu Val Asp Arg Trp Ile Glu Asp Leu Val Arg Pro Ile Ala
            100                 105                 110 cga cgc tac gtc gag gcg ttc gag tcc gac ggc agg gcc gat ctc gtc       384
Arg Arg Tyr Val Glu Ala Phe Glu Ser Asp Gly Arg Ala Asp Leu Val
        115                 120                 125 gcc cag ttc tgc gag ccg gtg agt gtg cgg tcg ctc ggt gat ctc ctc       432
Ala Gln Phe Cys Glu Pro Val Ser Val Arg Ser Leu Gly Asp Leu Leu
    130                 135                 140 gga ctg aag gac gtc agt tcg gac aaa ctg cgc gaa tgg ttc cac aaa       480
Gly Leu Lys Asp Val Ser Ser Asp Lys Leu Arg Glu Trp Phe His Lys
145                 150                 155                 160 ctg tcg gat tcg ttc acc aac gca gcg atg gac gag gac gga aac ttt       528
Leu Ser Asp Ser Phe Thr Asn Ala Ala Met Asp Glu Asp Gly Asn Phe
                165                 170                 175 ctg aac cag gaa cgt ttc gac gag ggc gac cgc gcc aag gag gag atc       576
Leu Asn Gln Glu Arg Phe Asp Glu Gly Asp Arg Ala Lys Glu Glu Ile
            180                 185                 190 cgt tcc gtc gtc gac ccg ctg atc gac cac tgg atc gag cat ccc gac       624
Arg Ser Val Val Asp Pro Leu Ile Asp His Trp Ile Glu His Pro Asp
        195                 200                 205 gac agc gcc atc tcg cac tgg ctg cac gac ggg atg ccc gaa ggg cag       672
Asp Ser Ala Ile Ser His Trp Leu His Asp Gly Met Pro Glu Gly Gln
    210                 215                 220 acg cgg gac cgc gac tac atc tac ccg acg ctg tac gtc ttc ctc ctc       720
Thr Arg Asp Arg Asp Tyr Ile Tyr Pro Thr Leu Tyr Val Phe Leu Leu
225                 230                 235                 240 ggc gcc atg cag gaa ccg gga cac gcc atg agt tcc acc ctg gca ggc       768
Gly Ala Met Gln Glu Pro Gly His Ala Met Ser Ser Thr Leu Ala Gly
                245                 250                 255 ctg ttc acc cgc ccc gaa cag ttc gaa gcc gtg gtg gac gaa ccg gga       816
Leu Phe Thr Arg Pro Glu Gln Phe Glu Ala Val Val Asp Glu Pro Gly
            260                 265                 270
```

```
ctc atc ccc cgc gcg atc gcc gaa ggg atg cgc tgg acc gcc ccg atc      864
Leu Ile Pro Arg Ala Ile Ala Glu Gly Met Arg Trp Thr Ala Pro Ile
    275                 280                 285 tgg tcc ggc acc gca cgt atc gcc aag cgc gac acc gtc gta tca gga      912
Trp Ser Gly Thr Ala Arg Ile Ala Lys Arg Asp Thr Val Val Ser Gly
290                 295                 300 atc gag atc agc gaa ggg tcg gtg gtc atg ctg tcc tac ggg tcg gcg      960
Ile Glu Ile Ser Glu Gly Ser Val Val Met Leu Ser Tyr Gly Ser Ala
305                 310                 315                 320 aac cac gac atc gac gtg ttc gac gcc ccc agc cgc tac gac ctg acc     1008
Asn His Asp Ile Asp Val Phe Asp Ala Pro Ser Arg Tyr Asp Leu Thr
                325                 330                 335 cgc ccg ccg ctc ccc cac ctc gcc ttc ggt gcc ggc aag cat gcc tgc     1056
Arg Pro Pro Leu Pro His Leu Ala Phe Gly Ala Gly Lys His Ala Cys
            340                 345                 350 gcg gga atc tac ttc gcg aac aac gtg agc cgc atc ggt ctc gaa gaa     1104
Ala Gly Ile Tyr Phe Ala Asn Asn Val Ser Arg Ile Gly Leu Glu Glu
        355                 360                 365 ctg ctc gag acc atc ccc aat ctc gag cgg gac act tcc gag gac gtc     1152
Leu Leu Glu Thr Ile Pro Asn Leu Glu Arg Asp Thr Ser Glu Asp Val
370                 375                 380 gaa ttc tgg ggt tgg ggc ttc cgc ggc ccg aag acc ctg cac gcc cgg     1200
Glu Phe Trp Gly Trp Gly Phe Arg Gly Pro Lys Thr Leu His Ala Arg
385                 390                 395                 400 tgg gag atc                                                         1209
Trp Glu Ile
```

<210> SEQ ID NO 6
<211> LENGTH: 403
<212> TYPE: PRT
<213> ORGANISM: Rhodococcus pyridinivorans AK37

<400> SEQUENCE: 6

```
Met Thr Ser Thr Leu Ser Trp Leu Asp Glu Ile Thr Met Glu Glu Leu
1               5                   10                  15

Glu Arg Asn Pro Tyr Pro Val Tyr Glu Arg Leu Arg Ala Glu Ala Pro
            20                  25                  30

Val Ala Phe Val Pro Val Leu Gly Ala Tyr Val Ala Ser Thr Thr Glu
        35                  40                  45

Ala Cys Arg Ala Val Ala Ala Gly Asp Asp Phe Asp Gly Ile Ile Thr
    50                  55                  60

Pro Ala Gly Gly Arg Thr Phe Gly His Pro Ala Ile Ile Gly Val Asn
65                  70                  75                  80

Gly Asp Ile His Arg Asp Leu Arg Ser Met Val Glu Pro Ala Leu Gln
                85                  90                  95

Pro Ala Glu Val Asp Arg Trp Ile Glu Asp Leu Val Arg Pro Ile Ala
            100                 105                 110

Arg Arg Tyr Val Glu Ala Phe Glu Ser Asp Gly Arg Ala Asp Leu Val
        115                 120                 125

Ala Gln Phe Cys Glu Pro Val Ser Val Arg Ser Leu Gly Asp Leu Leu
    130                 135                 140

Gly Leu Lys Asp Val Ser Ser Asp Lys Leu Arg Glu Trp Phe His Lys
145                 150                 155                 160

Leu Ser Asp Ser Phe Thr Asn Ala Ala Met Asp Glu Asp Gly Asn Phe
                165                 170                 175

Leu Asn Gln Glu Arg Phe Asp Glu Gly Asp Arg Ala Lys Glu Glu Ile
            180                 185                 190
```

```
Arg Ser Val Val Asp Pro Leu Ile Asp His Trp Ile Glu His Pro Asp
            195                 200                 205

Asp Ser Ala Ile Ser His Trp Leu His Asp Gly Met Pro Glu Gly Gln
        210                 215                 220

Thr Arg Asp Arg Asp Tyr Ile Tyr Pro Thr Leu Tyr Val Phe Leu Leu
225                 230                 235                 240

Gly Ala Met Gln Glu Pro Gly His Ala Met Ser Ser Thr Leu Ala Gly
                245                 250                 255

Leu Phe Thr Arg Pro Glu Gln Phe Glu Ala Val Val Asp Pro Gly
            260                 265                 270

Leu Ile Pro Arg Ala Ile Ala Glu Gly Met Arg Trp Thr Ala Pro Ile
        275                 280                 285

Trp Ser Gly Thr Ala Arg Ile Ala Lys Arg Asp Thr Val Val Ser Gly
        290                 295                 300

Ile Glu Ile Ser Glu Gly Ser Val Val Met Leu Ser Tyr Gly Ser Ala
305                 310                 315                 320

Asn His Asp Ile Asp Val Phe Asp Ala Pro Ser Arg Tyr Asp Leu Thr
                325                 330                 335

Arg Pro Pro Leu Pro His Leu Ala Phe Gly Ala Gly Lys His Ala Cys
            340                 345                 350

Ala Gly Ile Tyr Phe Ala Asn Asn Val Ser Arg Ile Gly Leu Glu Glu
        355                 360                 365

Leu Leu Glu Thr Ile Pro Asn Leu Glu Arg Asp Thr Ser Glu Asp Val
        370                 375                 380

Glu Phe Trp Gly Trp Gly Phe Arg Gly Pro Lys Thr Leu His Ala Arg
385                 390                 395                 400

Trp Glu Ile

<210> SEQ ID NO 7
<211> LENGTH: 990
<212> TYPE: DNA
<213> ORGANISM: Rhodococcus pyridinivorans AK37
<220> FEATURE:
<221> NAME/KEY: CDS
<222> LOCATION: (1)..(990)

<400> SEQUENCE: 7 atg ccg tac aca ctc acc gcg ggc acc ggc gtc gtt ccc tgc gaa ccc     48
Met Pro Tyr Thr Leu Thr Ala Gly Thr Gly Val Val Pro Cys Glu Pro
1               5                   10                  15 ggt cgg acg gtg ctg gaa gcg ttc ctg cgc aac ggc aac tgg atg ccc     96
Gly Arg Thr Val Leu Glu Ala Phe Leu Arg Asn Gly Asn Trp Met Pro
            20                  25                  30 aac tcc tgc aac cag gga acc tgc ggc acc tgc aag atc aag gtc ctc    144
Asn Ser Cys Asn Gln Gly Thr Cys Gly Thr Cys Lys Ile Lys Val Leu
        35                  40                  45 gac ggc gaa ctc gat cat cgg aac tcg ccg gag gag acg ctc acc gcc    192
Asp Gly Glu Leu Asp His Arg Asn Ser Pro Glu Glu Thr Leu Thr Ala
    50                  55                  60 gac gaa ctc gcg gcc gga ttc gtc ctc gcg tgc cag gcc acc ccg cgc    240
Asp Glu Leu Ala Ala Gly Phe Val Leu Ala Cys Gln Ala Thr Pro Arg
65                  70                  75                  80 ggc gac gtc gcc ttc gag acc ccc gca acg gag gaa ccc gcc ggc acg    288
Gly Asp Val Ala Phe Glu Thr Pro Ala Thr Glu Glu Pro Ala Gly Thr
                85                  90                  95 cac gtg ctg cgc gac gtc gtc gtc acc gtc acc gag gta cgc gac atc    336
His Val Leu Arg Asp Val Val Val Thr Val Thr Glu Val Arg Asp Ile
            100                 105                 110
```

```
gcc gcc gac aca cgc aag gtg ttg ctc acc gcc gac gaa ccg ctc gag      384
Ala Ala Asp Thr Arg Lys Val Leu Leu Thr Ala Asp Glu Pro Leu Glu
        115                 120                 125 ttc tcg gcc ggg cag tac gtg gag gtg aca gtt ccc ggg acc gag atc      432
Phe Ser Ala Gly Gln Tyr Val Glu Val Thr Val Pro Gly Thr Glu Ile
130                 135                 140 cga cgg cag tac tca ctc gcg aat ccg ccc tcc gag gcc aaa gag ctc      480
Arg Arg Gln Tyr Ser Leu Ala Asn Pro Pro Ser Glu Ala Lys Glu Leu
145                 150                 155                 160 gaa ctg cac atc cgc cgg caa ccc ggt gga gtc gcg agc gaa tgg gtc      528
Glu Leu His Ile Arg Arg Gln Pro Gly Gly Val Ala Ser Glu Trp Val
                165                 170                 175 ttc gag cgc atc gac gtg ggt gaa cgc gtg acc gtc acc ggc ccg tac      576
Phe Glu Arg Ile Asp Val Gly Glu Arg Val Thr Val Thr Gly Pro Tyr
            180                 185                 190 ggc gac ttc acc ttc gat ctg gag ggc acc gac ccg atc gtc ctg ctc      624
Gly Asp Phe Thr Phe Asp Leu Glu Gly Thr Asp Pro Ile Val Leu Leu
        195                 200                 205 ggc ggt ggg acg ggc ctc gcc ccg ctc gag gcc atc gtc cgg cag gcg      672
Gly Gly Gly Thr Gly Leu Ala Pro Leu Glu Ala Ile Val Arg Gln Ala
210                 215                 220 ctc tcc ctc gtc ccc gac cgg cag atc ctg ctc tac cac ggg gtc cgt      720
Leu Ser Leu Val Pro Asp Arg Gln Ile Leu Leu Tyr His Gly Val Arg
225                 230                 235                 240 acc tgc gcg gac ctg tac gac gtc gag ttt ctc cgc gaa ctg gag acc      768
Thr Cys Ala Asp Leu Tyr Asp Val Glu Phe Leu Arg Glu Leu Glu Thr
                245                 250                 255 cgt cat cac ggt ttc cgc tac atc acc tgc gtg agc agg gag agc ggc      816
Arg His His Gly Phe Arg Tyr Ile Thr Cys Val Ser Arg Glu Ser Gly
            260                 265                 270 gga gac cgc gac gga tac gtc acc gac gcc ttc ctc gag gac gtc gcg      864
Gly Asp Arg Asp Gly Tyr Val Thr Asp Ala Phe Leu Glu Asp Val Ala
        275                 280                 285 tcc gcg aag gag ttc acc ggt tac atc tgc gga tcg gac gcg ttc gtc      912
Ser Ala Lys Glu Phe Thr Gly Tyr Ile Cys Gly Ser Asp Ala Phe Val
290                 295                 300 gag gca tcg gtg aag gcg ttc aag cgt cgc cgc atg tcg ccg cga cgc      960
Glu Ala Ser Val Lys Ala Phe Lys Arg Arg Arg Met Ser Pro Arg Arg
305                 310                 315                 320 atc cgg cgc gaa cgg ttc acc ccg gcc ggc                              990
Ile Arg Arg Glu Arg Phe Thr Pro Ala Gly
                325                 330

<210> SEQ ID NO 8
<211> LENGTH: 330
<212> TYPE: PRT
<213> ORGANISM: Rhodococcus pyridinivorans AK37

<400> SEQUENCE: 8

Met Pro Tyr Thr Leu Thr Ala Gly Thr Gly Val Val Pro Cys Glu Pro
1               5                   10                  15

Gly Arg Thr Val Leu Glu Ala Phe Leu Arg Asn Gly Asn Trp Met Pro
            20                  25                  30

Asn Ser Cys Asn Gln Gly Thr Cys Gly Thr Cys Lys Ile Lys Val Leu
        35                  40                  45

Asp Gly Glu Leu Asp His Arg Asn Ser Pro Glu Glu Thr Leu Thr Ala
    50                  55                  60

Asp Glu Leu Ala Ala Gly Phe Val Leu Ala Cys Gln Ala Thr Pro Arg
65                  70                  75                  80
```

```
Gly Asp Val Ala Phe Glu Thr Pro Ala Thr Glu Pro Ala Gly Thr
                85                  90                  95

His Val Leu Arg Asp Val Val Thr Val Thr Glu Val Arg Asp Ile
            100                 105                 110

Ala Ala Asp Thr Arg Lys Val Leu Leu Thr Ala Asp Glu Pro Leu Glu
            115                 120                 125

Phe Ser Ala Gly Gln Tyr Val Glu Val Thr Val Pro Gly Thr Glu Ile
            130                 135                 140

Arg Arg Gln Tyr Ser Leu Ala Asn Pro Pro Ser Glu Ala Lys Glu Leu
145                 150                 155                 160

Glu Leu His Ile Arg Arg Gln Pro Gly Gly Val Ala Ser Glu Trp Val
                165                 170                 175

Phe Glu Arg Ile Asp Val Gly Glu Arg Val Thr Val Thr Gly Pro Tyr
            180                 185                 190

Gly Asp Phe Thr Phe Asp Leu Glu Gly Thr Asp Pro Ile Val Leu Leu
            195                 200                 205

Gly Gly Gly Thr Gly Leu Ala Pro Leu Glu Ala Ile Val Arg Gln Ala
210                 215                 220

Leu Ser Leu Val Pro Asp Arg Gln Ile Leu Leu Tyr His Gly Val Arg
225                 230                 235                 240

Thr Cys Ala Asp Leu Tyr Asp Val Phe Leu Arg Glu Leu Glu Thr
                245                 250                 255

Arg His His Gly Phe Arg Tyr Ile Thr Cys Val Ser Arg Glu Ser Gly
                260                 265                 270

Gly Asp Arg Asp Gly Tyr Val Thr Asp Ala Phe Leu Glu Asp Val Ala
            275                 280                 285

Ser Ala Lys Glu Phe Thr Gly Tyr Ile Cys Gly Ser Asp Ala Phe Val
            290                 295                 300

Glu Ala Ser Val Lys Ala Phe Lys Arg Arg Met Ser Pro Arg Arg
305                 310                 315                 320

Ile Arg Arg Glu Arg Phe Thr Pro Ala Gly
                325                 330

<210> SEQ ID NO 9
<211> LENGTH: 1209
<212> TYPE: DNA
<213> ORGANISM: Rhodococcus jostii
<220> FEATURE:
<221> NAME/KEY: CDS
<222> LOCATION: (1)..(1209)

<400> SEQUENCE: 9 atg acc gcc acc ctg tct tgg atc gac gag atc acg atg acg gaa ctc      48
Met Thr Ala Thr Leu Ser Trp Ile Asp Glu Ile Thr Met Thr Glu Leu
1               5                   10                  15 gag cgc aac ccg tac ccc gtc tac gag cgg ctg cgc gcc gag gcg ccg      96
Glu Arg Asn Pro Tyr Pro Val Tyr Glu Arg Leu Arg Ala Glu Ala Pro
                20                  25                  30 ctg gcc tac gtg ccg gtc ctc ggc tcg ttc gtc gcg acc acc gcc gac     144
Leu Ala Tyr Val Pro Val Leu Gly Ser Phe Val Ala Thr Thr Ala Asp
            35                  40                  45 ctg tgc cgc acc atc gcc aac agc ccc gac ttc gag ggg atc atc acc     192
Leu Cys Arg Thr Ile Ala Asn Ser Pro Asp Phe Glu Gly Ile Ile Thr
    50                  55                  60 aaa gcc ggc ggc cgc acg ttc ggt cac cct gcg gtg atc ggc gtc aac     240
Lys Ala Gly Gly Arg Thr Phe Gly His Pro Ala Val Ile Gly Val Asn
65                  70                  75                  80
```

```
ggc gag atc cac cgc gat ctc cgc tcg atg gtc gac ccc gca ctg caa        288
Gly Glu Ile His Arg Asp Leu Arg Ser Met Val Asp Pro Ala Leu Gln
                85                  90                  95 ccg tcg gag gtg gac cgc tgg gtc gac gga ctc gtc cgc ccc atc gcg        336
Pro Ser Glu Val Asp Arg Trp Val Asp Gly Leu Val Arg Pro Ile Ala
            100                 105                 110 cgg cgc tac gtg gag cag ttc gag aac gac ggc aag gcc gat ctg gtc        384
Arg Arg Tyr Val Glu Gln Phe Glu Asn Asp Gly Lys Ala Asp Leu Val
        115                 120                 125 tcg cag tac tgc gaa ccc gtc agc gtg cgc gcg ctc ggt gac ctc ctg        432
Ser Gln Tyr Cys Glu Pro Val Ser Val Arg Ala Leu Gly Asp Leu Leu
    130                 135                 140 ggg ctg aac gag gtc agc tcg gac acg ttg cgc gac tgg ttc cac cgg        480
Gly Leu Asn Glu Val Ser Ser Asp Thr Leu Arg Asp Trp Phe His Arg
145                 150                 155                 160 ctg tcg aac tcc ttc acc aat gcc gga gtg gat gcg gac ggc gag ttc        528
Leu Ser Asn Ser Phe Thr Asn Ala Gly Val Asp Ala Asp Gly Glu Phe
                165                 170                 175 acg aac ccg gag gga ttc gtg cag ggc gac gag gcc aag gca gag atc        576
Thr Asn Pro Glu Gly Phe Val Gln Gly Asp Glu Ala Lys Ala Glu Ile
            180                 185                 190 cgg gcc gtc gtc gat ccg ctc atc gac aag tgg acc gtc cac ccc gac        624
Arg Ala Val Val Asp Pro Leu Ile Asp Lys Trp Thr Val His Pro Asp
        195                 200                 205 gac agc gcc atc tcg cac tgg ctg cac gac ggc atg ccc gaa gga cag        672
Asp Ser Ala Ile Ser His Trp Leu His Asp Gly Met Pro Glu Gly Gln
    210                 215                 220 gtc cgc gac cgc gag tac atc tac ccc acg ctc ttc gtc tac ctg ctg        720
Val Arg Asp Arg Glu Tyr Ile Tyr Pro Thr Leu Phe Val Tyr Leu Leu
225                 230                 235                 240 ggc gcg atg cag gaa ccc ggg cac gga atg gca tcg aca ctc gtg ggc        768
Gly Ala Met Gln Glu Pro Gly His Gly Met Ala Ser Thr Leu Val Gly
                245                 250                 255 ctg ttc acc cgc ccc gag cag ctc gag gcc gtc atc gac gag cct gcc        816
Leu Phe Thr Arg Pro Glu Gln Leu Glu Ala Val Ile Asp Glu Pro Ala
            260                 265                 270 ctg att ccg cgg gcg ata tcc gag gga atg cgc tgg acc tcc ccg atc        864
Leu Ile Pro Arg Ala Ile Ser Glu Gly Met Arg Trp Thr Ser Pro Ile
        275                 280                 285 tgg tcg gcc acg gcc cgc atc agc acc aag gac gtc acg ctc ggg gac        912
Trp Ser Ala Thr Ala Arg Ile Ser Thr Lys Asp Val Thr Leu Gly Asp
    290                 295                 300 gtg ttc ctt ccc gaa gga tcc gtg gtc ctg ttg tcc tac ggt tcg gcc        960
Val Phe Leu Pro Glu Gly Ser Val Val Leu Leu Ser Tyr Gly Ser Ala
305                 310                 315                 320 aac cac gac acc gcc gtc tac gac gcc ccc tcc gac tac gac atg acg       1008
Asn His Asp Thr Ala Val Tyr Asp Ala Pro Ser Asp Tyr Asp Met Thr
                325                 330                 335 cgc cct ccg ctc ccc cac ctg gcg ttc ggt tcc ggc aac cac gcg tgc       1056
Arg Pro Pro Leu Pro His Leu Ala Phe Gly Ser Gly Asn His Ala Cys
            340                 345                 350 gcg ggt atc tac ttc gcg aac cac gtc tgc cgc atc ggc ctg gag gag       1104
Ala Gly Ile Tyr Phe Ala Asn His Val Cys Arg Ile Gly Leu Glu Glu
        355                 360                 365 ttg ttc gag gcg atc ccg aac ctc gaa cgt gac tcc ggc gcg gac gtg       1152
Leu Phe Glu Ala Ile Pro Asn Leu Glu Arg Asp Ser Gly Ala Asp Val
    370                 375                 380 gag ttc tgg ggc tgg ggt ttc cgc ggc ccg acc gcc ctc cgg gcc acg       1200
Glu Phe Trp Gly Trp Gly Phe Arg Gly Pro Thr Ala Leu Arg Ala Thr
```

```
                385             390             395             400
               tgg gag gtg                                                          1209
               Trp Glu Val
```

<210> SEQ ID NO 10
<211> LENGTH: 403
<212> TYPE: PRT
<213> ORGANISM: Rhodococcus jostii

<400> SEQUENCE: 10

Met Thr Ala Thr Leu Ser Trp Ile Asp Glu Ile Thr Met Thr Glu Leu
1               5                   10                  15

Glu Arg Asn Pro Tyr Pro Val Tyr Glu Arg Leu Arg Ala Glu Ala Pro
            20                  25                  30

Leu Ala Tyr Val Pro Val Leu Gly Ser Phe Val Ala Thr Thr Ala Asp
        35                  40                  45

Leu Cys Arg Thr Ile Ala Asn Ser Pro Asp Phe Glu Gly Ile Ile Thr
50                  55                  60

Lys Ala Gly Gly Arg Thr Phe Gly His Pro Ala Val Ile Gly Val Asn
65                  70                  75                  80

Gly Glu Ile His Arg Asp Leu Arg Ser Met Val Asp Pro Ala Leu Gln
                85                  90                  95

Pro Ser Glu Val Asp Arg Trp Val Asp Gly Leu Val Arg Pro Ile Ala
            100                 105                 110

Arg Arg Tyr Val Glu Gln Phe Glu Asn Asp Gly Lys Ala Asp Leu Val
        115                 120                 125

Ser Gln Tyr Cys Glu Pro Val Ser Val Arg Ala Leu Gly Asp Leu Leu
130                 135                 140

Gly Leu Asn Glu Val Ser Ser Asp Thr Leu Arg Asp Trp Phe His Arg
145                 150                 155                 160

Leu Ser Asn Ser Phe Thr Asn Ala Gly Val Asp Ala Asp Gly Glu Phe
                165                 170                 175

Thr Asn Pro Glu Gly Phe Val Gln Gly Asp Glu Ala Lys Ala Glu Ile
            180                 185                 190

Arg Ala Val Val Asp Pro Leu Ile Asp Lys Trp Thr Val His Pro Asp
        195                 200                 205

Asp Ser Ala Ile Ser His Trp Leu His Asp Gly Met Pro Glu Gly Gln
210                 215                 220

Val Arg Asp Arg Glu Tyr Ile Tyr Pro Thr Leu Phe Val Tyr Leu Leu
225                 230                 235                 240

Gly Ala Met Gln Glu Pro Gly His Gly Met Ala Ser Thr Leu Val Gly
                245                 250                 255

Leu Phe Thr Arg Pro Glu Gln Leu Glu Ala Val Ile Asp Glu Pro Ala
            260                 265                 270

Leu Ile Pro Arg Ala Ile Ser Glu Gly Met Arg Trp Thr Ser Pro Ile
        275                 280                 285

Trp Ser Ala Thr Ala Arg Ile Ser Thr Lys Asp Val Thr Leu Gly Asp
290                 295                 300

Val Phe Leu Pro Glu Gly Ser Val Val Leu Ser Tyr Gly Ser Ala
305                 310                 315                 320

Asn His Asp Thr Ala Val Tyr Asp Ala Pro Ser Asp Tyr Asp Met Thr
                325                 330                 335

Arg Pro Pro Leu Pro His Leu Ala Phe Gly Ser Gly Asn His Ala Cys
            340                 345                 350

```
Ala Gly Ile Tyr Phe Ala Asn His Val Cys Arg Ile Gly Leu Glu Glu
            355                 360                 365

Leu Phe Glu Ala Ile Pro Asn Leu Glu Arg Asp Ser Gly Ala Asp Val
370                 375                 380

Glu Phe Trp Gly Trp Gly Phe Arg Gly Pro Thr Ala Leu Arg Ala Thr
385                 390                 395                 400

Trp Glu Val

<210> SEQ ID NO 11
<211> LENGTH: 993
<212> TYPE: DNA
<213> ORGANISM: Rhodococcus jostii
<220> FEATURE:
<221> NAME/KEY: CDS
<222> LOCATION: (1)..(993)

<400> SEQUENCE: 11 gtg acc ttc acc gtt tcg gtc gcc gcg gac agg gtg gaa tgc cgc ccc     48
Met Thr Phe Thr Val Ser Val Ala Ala Asp Arg Val Glu Cys Arg Pro
1               5                   10                  15 gac cag ccg ata ctc gac gct ttc ctc cgg ggc agc gtg tgg atg ccg     96
Asp Gln Pro Ile Leu Asp Ala Phe Leu Arg Gly Ser Val Trp Met Pro
            20                  25                  30 aac tcg tgc aac cag ggc acg tgc gga acg tgc aag ctg cgg gtc gtg    144
Asn Ser Cys Asn Gln Gly Thr Cys Gly Thr Cys Lys Leu Arg Val Val
        35                  40                  45 tcg gga tcg gtc gat cat ggg cgt tcg ccc gag gac acg ctc acc cag    192
Ser Gly Ser Val Asp His Gly Arg Ser Pro Glu Asp Thr Leu Thr Gln
    50                  55                  60 gcc gac cgc gag cag ggt ttc gcc ctg gcc tgc cag gcc aca ccg tgc    240
Ala Asp Arg Glu Gln Gly Phe Ala Leu Ala Cys Gln Ala Thr Pro Cys
65                  70                  75                  80 agt gac acc gtg gtg gaa cgc ctg gac acg gcg ccg gcg ggc acc gtc    288
Ser Asp Thr Val Val Glu Arg Leu Asp Thr Ala Pro Ala Gly Thr Val
                85                  90                  95 cac gcc ctg cgg gac ctc atc ggc acc gtg agt gcg atc gag gac gtc    336
His Ala Leu Arg Asp Leu Ile Gly Thr Val Ser Ala Ile Glu Asp Val
            100                 105                 110 gcc cgt gac acg cgg cgg gtt ctc gtc acg ctc gac agc ccg ctc gaa    384
Ala Arg Asp Thr Arg Arg Val Leu Val Thr Leu Asp Ser Pro Leu Glu
        115                 120                 125 ttc tcc gca ggg cag tac gtc gaa ctg cga gta ccc ggc acc gac cac    432
Phe Ser Ala Gly Gln Tyr Val Glu Leu Arg Val Pro Gly Thr Asp His
    130                 135                 140 tgc cgc cag tac tcg atg gcg aac acg ccg ggc gag tcg aaa cag ctc    480
Cys Arg Gln Tyr Ser Met Ala Asn Thr Pro Gly Glu Ser Lys Gln Leu
145                 150                 155                 160 gag ttc cac atc cgc agg caa ccg ggt gga gtc gcg acg gac ggt tgg    528
Glu Phe His Ile Arg Arg Gln Pro Gly Gly Val Ala Thr Asp Gly Trp
                165                 170                 175 gtc ttc ggc acg ctg tcc gtc ggc gag cga gtc gag atg acg ggg ccg    576
Val Phe Gly Thr Leu Ser Val Gly Glu Arg Val Glu Met Thr Gly Pro
            180                 185                 190 ctc ggc gac ttc cgt ctc gat ccg gag gac gag ggt ccg atg atc ctg    624
Leu Gly Asp Phe Arg Leu Asp Pro Glu Asp Glu Gly Pro Met Ile Leu
        195                 200                 205 ctc ggc ggc gga acc ggg ctt gcc ccg ctg aaa tcg atg gtc gcc cag    672
Leu Gly Gly Gly Thr Gly Leu Ala Pro Leu Lys Ser Met Val Arg Gln
    210                 215                 220 gca ctc acg gtc aca ccg gaa cgc gcg atc cac ctc tat cac ggc gtg    720
Ala Leu Thr Val Thr Pro Glu Arg Ala Ile His Leu Tyr His Gly Val
```

```
Ala Leu Thr Val Thr Pro Glu Arg Ala Ile His Leu Tyr His Gly Val
225                 230                 235                 240 cgg gaa gca gcc gac ctg tac gac gtc gac ctg ttt cgg gag tgg gaa       768
Arg Glu Ala Ala Asp Leu Tyr Asp Val Asp Leu Phe Arg Glu Trp Glu
                245                 250                 255 cgc gcg cac ccg ggg ttc cga tac gtt ccg tgt ctg agc gat tcg acg       816
Arg Ala His Pro Gly Phe Arg Tyr Val Pro Cys Leu Ser Asp Ser Thr
            260                 265                 270 tgg tcc ggc cgg acg ggc ttc gtc acc gac gcg ttc gtg gag gac ttc       864
Trp Ser Gly Arg Thr Gly Phe Val Thr Asp Ala Phe Val Glu Asp Phe
        275                 280                 285 gac acc tgt cgc ggc tac tcc ggg tac ctg tgc ggg ccg ccg gcg atg       912
Asp Thr Cys Arg Gly Tyr Ser Gly Tyr Leu Cys Gly Pro Pro Ala Met
    290                 295                 300 gtc gac gcc gga gtc aag gcg ttc aag cgc cgg cgc atg gct cct cga       960
Val Asp Ala Gly Val Lys Ala Phe Lys Arg Arg Arg Met Ala Pro Arg
305                 310                 315                 320 cgc atc ttc cgg gag aag ttc acg ccc gcc gcg                           993
Arg Ile Phe Arg Glu Lys Phe Thr Pro Ala Ala
                325                 330

<210> SEQ ID NO 12
<211> LENGTH: 331
<212> TYPE: PRT
<213> ORGANISM: Rhodococcus jostii

<400> SEQUENCE: 12

Met Thr Phe Thr Val Ser Val Ala Ala Asp Arg Val Glu Cys Arg Pro
1               5                   10                  15

Asp Gln Pro Ile Leu Asp Ala Phe Leu Arg Gly Ser Val Trp Met Pro
            20                  25                  30

Asn Ser Cys Asn Gln Gly Thr Cys Gly Thr Cys Lys Leu Arg Val Val
        35                  40                  45

Ser Gly Ser Val Asp His Gly Arg Ser Pro Glu Asp Thr Leu Thr Gln
    50                  55                  60

Ala Asp Arg Glu Gln Gly Phe Ala Leu Ala Cys Gln Ala Thr Pro Cys
65                  70                  75                  80

Ser Asp Thr Val Val Glu Arg Leu Asp Thr Ala Pro Ala Gly Thr Val
                85                  90                  95

His Ala Leu Arg Asp Leu Ile Gly Thr Val Ser Ala Ile Glu Asp Val
            100                 105                 110

Ala Arg Asp Thr Arg Arg Val Leu Val Thr Leu Asp Ser Pro Leu Glu
        115                 120                 125

Phe Ser Ala Gly Gln Tyr Val Glu Leu Arg Val Pro Gly Thr Asp His
    130                 135                 140

Cys Arg Gln Tyr Ser Met Ala Asn Thr Pro Gly Glu Ser Lys Gln Leu
145                 150                 155                 160

Glu Phe His Ile Arg Arg Gln Pro Gly Gly Val Ala Thr Asp Gly Trp
                165                 170                 175

Val Phe Gly Thr Leu Ser Val Gly Glu Arg Val Glu Met Thr Gly Pro
            180                 185                 190

Leu Gly Asp Phe Arg Leu Asp Pro Glu Asp Gly Pro Met Ile Leu
        195                 200                 205

Leu Gly Gly Gly Thr Gly Leu Ala Pro Leu Lys Ser Met Val Arg Gln
    210                 215                 220

Ala Leu Thr Val Thr Pro Glu Arg Ala Ile His Leu Tyr His Gly Val
225                 230                 235                 240
```

```
Arg Glu Ala Ala Asp Leu Tyr Asp Val Asp Leu Phe Arg Glu Trp Glu
                245                 250                 255

Arg Ala His Pro Gly Phe Arg Tyr Val Pro Cys Leu Ser Asp Ser Thr
            260                 265                 270

Trp Ser Gly Arg Thr Gly Phe Val Thr Asp Ala Phe Val Glu Asp Phe
        275                 280                 285

Asp Thr Cys Arg Gly Tyr Ser Gly Tyr Leu Cys Gly Pro Pro Ala Met
    290                 295                 300

Val Asp Ala Gly Val Lys Ala Phe Lys Arg Arg Met Ala Pro Arg
305                 310                 315                 320

Arg Ile Phe Arg Glu Lys Phe Thr Pro Ala Ala
                325                 330

<210> SEQ ID NO 13
<211> LENGTH: 29
<212> TYPE: DNA
<213> ORGANISM: Artificial Sequence
<220> FEATURE:
<223> OTHER INFORMATION: PCR Primer

<400> SEQUENCE: 13
gatatcattc aggacgagcc tcagactcc                                        29

<210> SEQ ID NO 14
<211> LENGTH: 36
<212> TYPE: DNA
<213> ORGANISM: Artificial Sequence
<220> FEATURE:
<223> OTHER INFORMATION: PCR Primer

<400> SEQUENCE: 14
ctctagagtg tgaaattgtt atccgctcac aattcc                                36

<210> SEQ ID NO 15
<211> LENGTH: 52
<212> TYPE: DNA
<213> ORGANISM: Artificial Sequence
<220> FEATURE:
<223> OTHER INFORMATION: PCR Primer

<400> SEQUENCE: 15
aacaatttca cactctagag aggaggacag ctatgacgac gaccgaacgg cc              52

<210> SEQ ID NO 16
<211> LENGTH: 36
<212> TYPE: DNA
<213> ORGANISM: Artificial Sequence
<220> FEATURE:
<223> OTHER INFORMATION: PCR Primer

<400> SEQUENCE: 16
ggctcgtcct gaatgatatc tcacgaggcc ggcgtg                                36

<210> SEQ ID NO 17
<211> LENGTH: 41
<212> TYPE: DNA
<213> ORGANISM: Artificial Sequence
<220> FEATURE:
<223> OTHER INFORMATION: PCR Primer

<400> SEQUENCE: 17
ggctcgtcct gaatgatatc tcacacctcc caggtgacgt g                          41
```

ENZYMES AND METHODS FOR DEALKYLATION OF SUBSTRATES

CROSS-REFERENCE TO RELATED APPLICATIONS

This application claims priority to U.S. Provisional Application No. 62/130,482, filed Mar. 9, 2015, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "14-54_ST25.txt," having a size in bytes of 56 kb and created on Mar. 8, 2016. Pursuant to 37 CFR § 1.52(e)(5), the information contained in the above electronic file is hereby incorporated by reference in its entirety.

BACKGROUND

Lignocellulosic biomass represents a vast resource for the production of renewable transportation fuels and chemicals to offset and replace current fossil fuel usage. The lignin component of lignocellulosic biomass is an energy-dense, heterogeneous alkyl-aromatic polymer comprised of phenylpropanoid monomers used by plants for water transport and defense, and it is the second most abundant biopolymer on Earth after cellulose. Lignin is typically underutilized in most selective conversion processes for biofuel production. In the production of fuels and chemicals from biomass, lignin is typically burned for process heat because its inherent heterogeneity and recalcitrance make it difficult to selectively upgrade the monomers to value added products. This limited ability to utilize lignin, despite being the most energy dense polymer in the plant cell wall, is primarily due to its inherent heterogeneity and recalcitrance. Guaiacol (2-methoxyphenol) is one of many products that result from lignin depolymerization.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide methods for removing an alkyl group from an aromatic substrate by contacting material containing the aromatic substrate with a cytochrome P450 polypeptide and a reductase polypeptide to generate a dealkylation product.

In various embodiments, the contacting step comprises culturing a microorganism with the material containing the aromatic substrate where the microorganism expresses an exogenous gene encoding a cytochrome P450 polypeptide or a reductase polypeptide.

In some embodiments, the aromatic substrate comprises guaiacol, anisole or guaethol; comprises products of lignin depolymerization, or comprises a pyrolysis oil or bio-oil.

In certain embodiments, at least one of the cytochrome P450 polypeptide or the reductase polypeptide is from a bacterium, such as a bacterium from the genera *Amycolatopsis* or *Rhodococcus*.

In exemplary embodiments, the cytochrome P450 polypeptide has an amino acid sequence at least 90% identical to SEQ ID NO:2. In others, the reductase polypeptide has an amino acid sequence at least 90% identical to SEQ ID NO:4.

In further embodiments, the dealkylation product is catechol or phenol.

In some embodiments, the methods further comprise isolating the dealkylation product.

Additional embodiments provide isolated cDNA molecules encoding cytochrome P450 polypeptides that have amino acid sequences at least 90% identical to SEQ ID NO:2 or encoding reductase polypeptides that have amino acid sequences at least 90% identical to SEQ ID NO:4. In certain embodiments, the polypeptides have amino acid sequences identical to SEQ ID NO:2 or SEQ ID NO:4.

In various embodiments, the cDNA molecules further comprise an exogenous promoter operably linked to the cDNA molecules. Other embodiments provide expression vector comprising the cDNA molecules and host cells that express a recombinant polypeptide encoded by the cDNA molecules, including host cells that are strains of *Pseudomonas* such as *P. putida*.

Other embodiments provide isolated cytochrome P450 polypeptides and reductase polypeptides encoded by the cDNA molecules.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 2 shows the nucleic acid sequence (A) and amino acid sequence (B) of a cytochrome P450 O-dealkylase from *Amycolatopsis* sp. ATCC 39116.

FIG. 3 shows the nucleic acid sequence (A) and amino acid sequence (B) of a reductase from *Amycolatopsis* sp. ATCC 39116.

DETAILED DESCRIPTION

Figures 2, 2A, 2B:
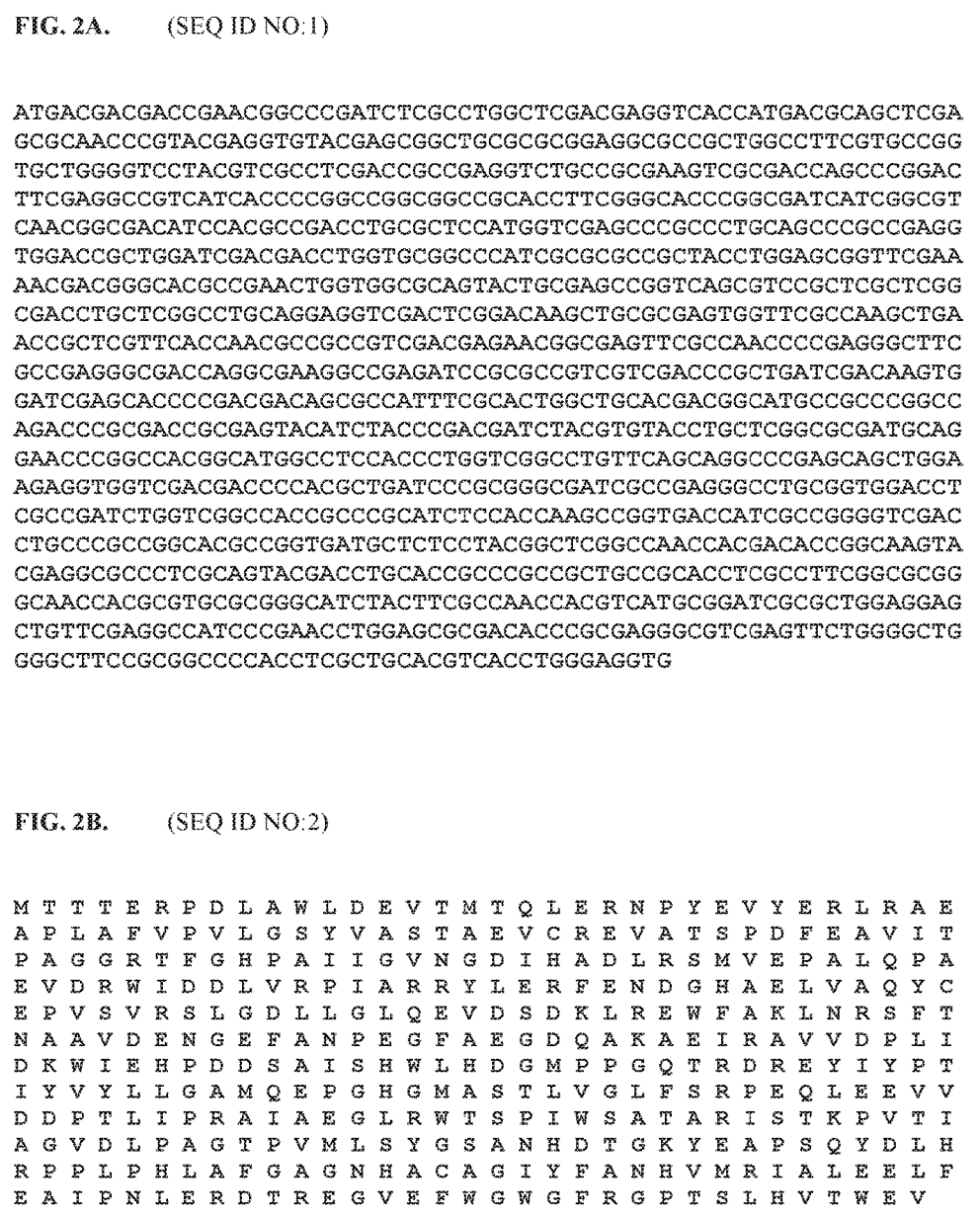
Figure 1:
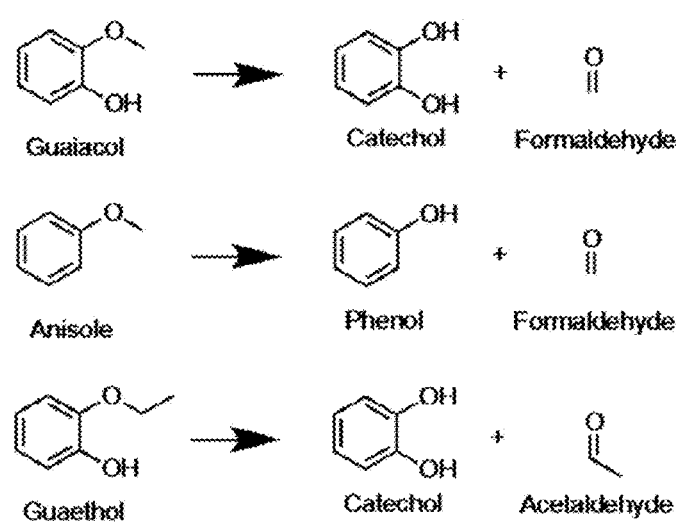
FIG. 1 shows exemplary dealkylation reactions catalyzed by the two component cytochrome P450 system.

Disclosed herein are enzymes, organisms expressing these enzymes, and methods useful for the dealkylation of aromatic substrates, including the conversion of guaiacol or guaethol to catechol and the conversion of anisole to phenol. Methods of converting aromatic substrates found in lignin-based feedstocks such as pyrolysis oil into catechol and phenol are also disclosed. FIGS. 2 and 3 present the nucleic acid sequences and amino acid sequences of two enzymes useful for the enzymatic conversion described herein.

Guaiacol (2-methoxyphenol), anisole (methoxybenzene), and guaethol (2-ethoxyphenol) are common products of lignin depolymerization, and the conversion of guaiacol or guaethol to catechol (1,2-dihydroxybenzene) allows the more efficient use of products derived from lignin.

Disclosed herein are cytochrome P450 O-dealkylases and reductases that catalyze reactions such as the O-demethylation of guaiacol to catechol, the O-demethylation of anisole to phenol, and the O-deethylation of guaethol to catechol. Generally, dealkylation is the removal of an alkyl group from a substrate, such as the removal of a methyl group to convert guaiacol to catechol and formaldehyde. These enzymes have activity not only on guaiacol, but also on anisole and guaethol. O-dealkylases may remove methyl, ethyl, propyl, butyl and other alkyl groups of the general formula $C_nH_{2n+1}$ from substrates. Another O-dealkylase activity may be to perform ether bond cleavage on aromatic compounds. In various embodiments, the enzymes may be from the CYP255 family of cytochrome P450 enzymes.

Some bacterial cytochrome P450 enzymes cooperate with one or two partner proteins, usually a reductase and a ferredoxin, that transfer electrons from a cofactor such as NAD(P)H to the cytochrome, though there are variations on this throughout prokaryotes and eukaryotes. In certain embodiments, the reductase may comprise a 2Fe-2S ferredoxin domain, a flavin adenine dinucleotide (FAD) binding region, a nicotinamide adenine dinucleotide (NAD) binding region or combinations thereof. For example, the reductase represented by SEQ ID NO:4 comprises an N-terminal 2Fe-2S ferredoxin domain followed by a FAD and NAD binding region with homology to ferredoxin-NADPH reductase (FNR) type oxidoreductases. This domain architecture is novel for a cytochrome P450 reductase, and the presence of both ferredoxin and NAD binding domains may indicate the reductase and the cytochrome P450, whose genes are natively clustered and transcribed together, form a two-component cytochrome P450 system.

The combination of both the cytochrome P450 and reductase polypeptides may be used as a two-component P450 system for dealkylating aromatic substrates, including demethylating guaiacol to produce catechol. For example, nucleic acid molecules encoding SEQ ID NOs: 2 and 4 encode a two-component cytochrome P450 system with guaiacol O-demethylase activity, as well as activity on other substrates including anisole (methoxybenzene), guaethol (2-ethoxyphenol), 2-propoxyphenol, and other substituted O-alkoxyphenols. Additional examples of two-component systems that exhibit these enzymatic activities include the cytochrome P450 (EHK82401; SEQ ID NO:6) and reductase (EHK82400; SEQ ID NO:8) polypeptides from *Rhodococcus pyridinivorans* AK37 and the cytochrome P450 (WP_011595125; SEQ ID NO:10) and reductase (WP_011595126; SEQ ID NO:12) polypeptides from *Rhodococcus jostii*.

In addition to the enzymes described in FIGS. 2 and 3 and in the Sequence Listing, other suitable enzymes for aromatic substrate conversion include enzymes from *Rhodococcus pyridinivorans* strains SB3094 (e.g., YP_008987954.1) and AK37 (e.g., WP_006553158.1), *Rhodococcus jostii* RHA1 (e.g., YP_702345.1) and *Amycolatopsis* sp. ATCC 39116 (previously known as *Streptomyces setonii* or *Streptomyces griseus* strain 75iv2). In some embodiments, the cytochrome P450 or reductase polypeptide may be from a species of the genera *Rhodococcus* (e.g., *R. pyridinivorans* or *R. jostii*) or *Amycolatopsis* (e.g., *Amycolatopsis* sp. ATCC 39116). Additional exemplary cytochrome P450 and reductase polypeptides are provided in Table 1 below.

In various embodiments, the cytochrome P450 and reductase polypeptides may be from microorganisms such as bacteria, yeast or fungi. Exemplary bacteria include species from the family Pseudonocardiaceae or species from the genera *Rhodococcus*, *Amycolatopsis*, *Pimelobacter*, *Gordonia*, *Pseudonocardia*, *Saccharomonospora*, *Corynebacterium*, *Actinopolyspora*, *Nocardia*, *Saccharopolyspora*, *Nocardioides*, or *Granulicoccus*. Though specific examples are provided herein, other examples of microbial cytochrome P450 and reductase polypeptides are within the scope of this disclosure.

Cytochrome P450 polypeptides may be combined with reductase polypeptides to form a functional two-component complex capable of dealkylating an aromatic substrate. One of both of the polypeptides may be used in purified form. One of both of the polypeptides may be expressed by a microbial biocatalyst to carry out dealkylation. A biocatalyst host cell may express one or more of the polypeptides, or one or more of the polypeptides may be added exogenously to a biocatalyst culture. The cytochrome P450 and reductase polypeptides may be from the same organism or from different organisms, and various combinations may be created and tested for enzymatic activity.

TABLE 1

| Cytochrome P450s and Reductases | | | |
|---|---|---|---|
| Reductases | | Cytochrome P450s | |
| Organism | Accession No. | Organism | Accession No. |
| *Rhodococcus pyridinivorans* | WP_006553157.1 | *Rhodococcus pyridinivorans* | WP_024102362.1 |
| *Rhodococcus pyridinivorans* | WP_041803486.1 | *Rhodococcus pyridinivorans* | WP_060652632.1 |
| *Rhodococcus rhodochrous* | WP_016691158.1 | *Rhodococcus rhodochrous* | WP_016691159.1 |

TABLE 1-continued

Cytochrome P450s and Reductases

| Reductases | | Cytochrome P450s | |
| --- | --- | --- | --- |
| Organism | Accession No. | Organism | Accession No. |
| Rhodococcus rhodochrous | WP_059382679.1 | Rhodococcus ruber | WP_003934526.1 |
| Rhodococcus ruber | WP_003934527.1 | Gordonia rhizosphera | WP_006338923.1 |
| Rhodococcus aetherivorans | WP_029546517.1 | Gordonia bronchialis | WP_012835331.1 |
| Rhodococcus wratislaviensis | WP_037225711.1 | Gordonia namibiensis | WP_006865278.1 |
| Rhodococcus opacus | WP_005261032.1 | Gordonia alkanivorans | WP_006358554.1 |
| Rhodococcus imtechensis | WP_007297192.1 | Gordonia rubripertincta | WP_005194215.1 |
| Rhodococcus jostii | WP_054246359.1 | Gordonia terrae | WP_004020850.1 |
| Pimelobacter simplex | WP_038682083.1 | Rhodococcus wratislaviensis | WP_037225709.1 |
| Amycolatopsis methanolica | WP_017982757.1 | Rhodococcus jostii | WP_011595125.1 |
| Amycolatopsis orientalis | WP_043838556.1 | Rhodococcus imtechensis | WP_007297193.1 |
| Amycolatopsis sp. ATCC 39116 | WP_020419854.1 | Rhodococcus opacus | WP_012689299.1 |
| Pseudonocardia autotrophica | WP_037048581.1 | Amycolatopsis sp. ATCC39116 | WP_020419855.1 |
| Gordonia alkanivorans | WP_006358553.1 | Amycolatopsis methanolica | WP_017982758.1 |
| Gordonia sp. KTR9 | WP_014924832.1 | Gordonia polyisoprenivorans | WP_006367698.1 |
| Gordonia namibiensis | WP_006865279.1 | Gordonia polyisoprenivorans | WP_014360659.1 |
| Gordonia terrae | WP_004020851.1 | Saccharomonospora cyanea | WP_005457512.1 |
| Gordonia rubripertincta | WP_039879854.1 | Pseudonocardia autotrophica | WP_037048579.1 |
| Saccharomonospora cyanea | WP_005457513.1 | Gordonia desulfuricans | WP_059037021.1 |
| Gordonia polyisoprenivorans | WP_014360660.1 | Nocardia farcinica | WP_011208761.1 |
| Gordonia bronchialis | WP_012835332.1 | Saccharopolyspora rectivirgula | WP_029722698.1 |
| Gordonia rhizosphera | WP_006338924.1 | Nocardioides luteus | WP_045548139.1 |
| Gordonia rubripertincta | GAB83512.1 | Amycolatopsis orientalis | WP_043838558.1 |
| Corynebacterium halotolerans | WP_015400585.1 | Amycolatopsis orientalis | WP_037363061.1 |
| Actinopolyspora halophila | WP_017975556.1 | Pseudonocardia sp. AL041005-10 | ALE78654.1 |
| Gordonia sputi | WP_039856233.1 | Granulicoccus phenolivorans | WP_035757215.1 |
| Rhodococcus wratislaviensis IFP 2016 | ELB87463.1 | Pimelobacter simplex | WP_038682080.1 |
| Rhodococcus imtechensis | WP_007296205.1 | Gordonia amicalis | WP_024500047.1 |
| Gordonia desulfuricans | WP_059037022.1 | | |

Also presented are microorganisms engineered to express the enzymes disclosed herein and their use to biologically dealkylate aromatic substrates. Dealkylation may be carried out be culturing such microorganisms with a material containing aromatic substrates (e.g., guaiacol, guaethol or anisole) and allowing the microorganisms to enzymatically complete the conversion. Although the Examples presented herein exemplify the use of the bacterium *P. putida*, any microorganism capable of carrying out the dealkylation of the substrate through the addition of enzymes disclosed herein may be suitable. Exemplary microorganisms include bacteria, such as those from the genus *Pseudomonas*. Specific examples include strains of *Pseudomonas putida*, such as *P. putida* KT2440.

Aromatic substrate-containing materials may be contacted with enzymes disclosed herein to dealkylate the substrate. As used herein, "aromatic substrate-containing materials" means any natural or processed materials comprising detectable amounts of compounds such as guaiacol, guaethol or anisole. These may be derived from many sources, including lignocellulose, lignin, or oils derived from the pyrolysis of biomass of other lignocellulose or cellulose sources.

Suitable enzymes may be derived from microorganisms such as bacteria, fungi, yeast or the like via cell lysis and isolation techniques, or produced recombinantly. In some embodiments, a microorganism expressing the enzyme may be used directly as a biocatalyst to covert the aromatic substrate.

Enzymes described herein may be used as purified recombinant enzyme or as culture broths from cells that naturally produce the enzyme or that have been engineered to produce the enzyme. Enzymes can be added exogenously, or may be expressed and secreted directly from a microbial biocatalyst, or used internally by the microbial biocatalyst. Suitable organisms for enzyme expression include aerobic microorganisms such as aerobic bacteria.

Bio-oils and other aromatic substrate-containing materials may be contacted with enzymes at a concentration and a temperature for a time sufficient to achieve the desired amount of dealkylation. Suitable times for dealkylation range from a few hours to several days, and may be selected to achieve a desired amount of conversion. Exemplary reaction times include 1, 2, 3, 4, 5, 6, 7, 8, 9, 10, 11, or 12 hours; and 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 days. In some embodiments, reaction times may be one or more weeks.

The resulting catechol, phenol, and the like may be further converted to products such as higher alcohols, hydrocarbons, or other advanced fuels via biological or chemical pathways, or combination thereof. Catechol, phenol and other products may be recovered or isolated from cells, cell cultures or reactions by standard separation techniques for further upgrading. Dealkylation products may also be further metabolized by biocatalyst cells in the culture to additional products metabolically derived from a dealkylation product. These additional products may in turn be isolated from cells, cell cultures or reactions by standard separation techniques and may be further upgraded to additional fuels and chemicals.

Methods of fractionating, isolating or purifying dealkylation products (or further upgraded products) include a variety of biochemical engineering unit operations. For example, the reaction mixture or cell culture lysate may be filtered to separate solids from products present in a liquid portion. Dealkylation products may be further extracted from a solvent and/or purified using conventional methods. Exemplary methods for purification/isolation/separation of dealkylation products include at least one of affinity chromatography, ion exchange chromatography, solvent extraction, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, and/or or reversed-phase HPLC.

Pyrolysis offers a straightforward approach for the deconstruction of plant cell wall polymers into pyrolysis oil or bio-oil, which may be fractionated and subsequently used in biological approaches to selectively upgrade some of the resulting fractions. Lignocellulose or lignin-containing materials may be subjected to pyrolysis processes to generate oils containing aromatic substrates. Exemplary lignocellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

SEQ ID NOS: 1, 3, 5, 7, 9 and 11 provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning or assembling) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional cytochrome P450 O-dealkylase or reductase. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode the polypeptides that function as an O-dealkylase or a reductase or functional equivalents thereof. A functional equivalent includes fragments or variants of these that exhibit the ability to function as an O-dealkylase or a reductase. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T. viride, T. koningii,* or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori,* or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Exemplary culture/fermentation conditions and reagents are provided in the Examples that follow. Media may be supplemented with aromatic substrates like guaiacol, guaethol or anisole for dealkylation reactions.

The nucleic acid molecules described herein encode the enzymes with amino acid sequences such as those represented by SEQ ID NOS:2, 4, 6, 8, 10 and 12. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented in SEQ ID NOS:2, 4, 6, 8, 10 and 12, or may include up to a certain integer number of amino acid alterations. Such protein or polypeptide variants retain functionality as a cytochrome P450 O-dealkylase or a reductase, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences set forth in SEQ ID NOS:2, 4, 6, 8, 10 and 12 and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

EXAMPLES

Example 1

Enzyme Cloning

The primers listed in Table 2 were used in the gene amplifications described below.

TABLE 2

Nucleic Acid Sequences of Primers

| Primer | Sequence (5'-3') | SEQ ID NO. |
|---|---|---|
| oCJ160 | GATATCATTCAGGACGAGCCTCAGACTCC | SEQ ID NO: 13 |
| oCJ161 | CTCTAGAGTGTGAAATTGTTATCCGCTCACAATTCC | SEQ ID NO: 14 |
| oCJ169 | AACAATTTCACACTCTAGAGAGGAGGACAGCTATGACGACGACCGAACGGCC | SEQ ID NO: 15 |
| oCJ170 | GGCTCGTCCTGAATGATATCTCACGAGGCCGGCGTG | SEQ ID NO: 16 |

TABLE 2-continued

Nucleic Acid Sequences of Primers

| Primer | Sequence (5'-3') | SEQ ID NO. |
|---|---|---|
| oCJ206 | GGCTCGTCCTGAATGATATCTCACACCTCCCAGGTGACGTG | SEQ ID NO: 17 |

The genes encoding the cytochrome P450 protein and the co-transcribed reductase were amplified from *Amycolatopsis* sp. ATCC 39116 DNA using primers oCJ169 and oCJ170 (see Table 2) and the product assembled using Gibson Assembly Master Mix (New England BioLabs) into the broad host-range vector pBTL-2, which was amplified using primers oCJ160 and oCJ161, resulting in pCJ021. pBTL-2 (a gift from Ryan Gill; Addgene plasmid #22806) is a broad host-range vector that drives expression of inserted genes using the lac promoter, which is constitutively expressed in *Pseudomonas putida* KT2440. The cytochrome P450 gene alone was also amplified using oCJ169 and oCJ206 and assembled it into the same vector (resulting in pCJ024). pCJ021 was then transformed into *P. putida* KT2440 to generate *P. putida* KT2440/pCJ021.

Example 2

HPLC Analyses

HPLC analysis was performed by injecting 6 μL of 0.2 μm filtered culture supernatant onto an Agilent 1100 series system equipped with a Phenomenex Rezex RFQ-Fast Acid H+ (8%) column and a cation H+ guard cartridge (Bio-Rad Laboratories) at 85° C. run using a mobile phase of 0.01 N sulfuric acid at a flow rate of 1.0 mL/min and a diode array detector to measure absorbance at 210 nm. Analytes were identified by comparing retention times and spectral profiles with pure standards. HPLC chromatograms show milliabsorbance units (mAU) on the Y axis and retention time (minutes) on the X axis.

Example 3

Conversion of Guaiacol, Anisole and Guaethol

Figure 4:
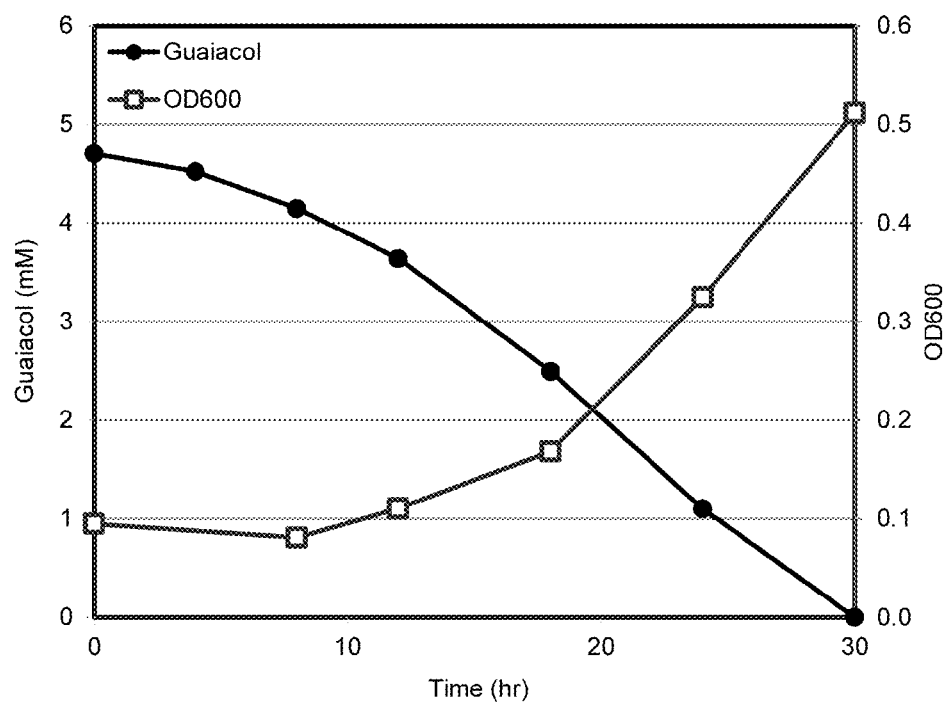
FIG. 4 shows growth by *P. putida* KT2440 engineered to express a cytochrome P450 O-dealkylase and a reductase (*P. putida* KT2440/pCJ021) on media containing guaiacol.

*P. putida* KT2440 can readily metabolize catechol for growth, so a functional enzyme with O-dealkylase activity would convert guaiacol or guaethol to catechol and enable this organism to metabolize guaiacol or guaethol for growth, which it is not natively capable of *P. putida* KT2440 transformed with pCJ021 (KT2440/pCJ021) was capable of growth in M9 minimal medium containing 5 mM guaiacol as the sole source of carbon and energy, metabolizing the guaiacol completely and reaching an $OD_{600}$ of just over 0.5 (FIG. 4). Native *P. putida* KT2440 and *P. putida* KT2440 transformed with pCJ024 were included in this experiment, but neither of these strains was able to metabolize guaiacol.

Figure 5:
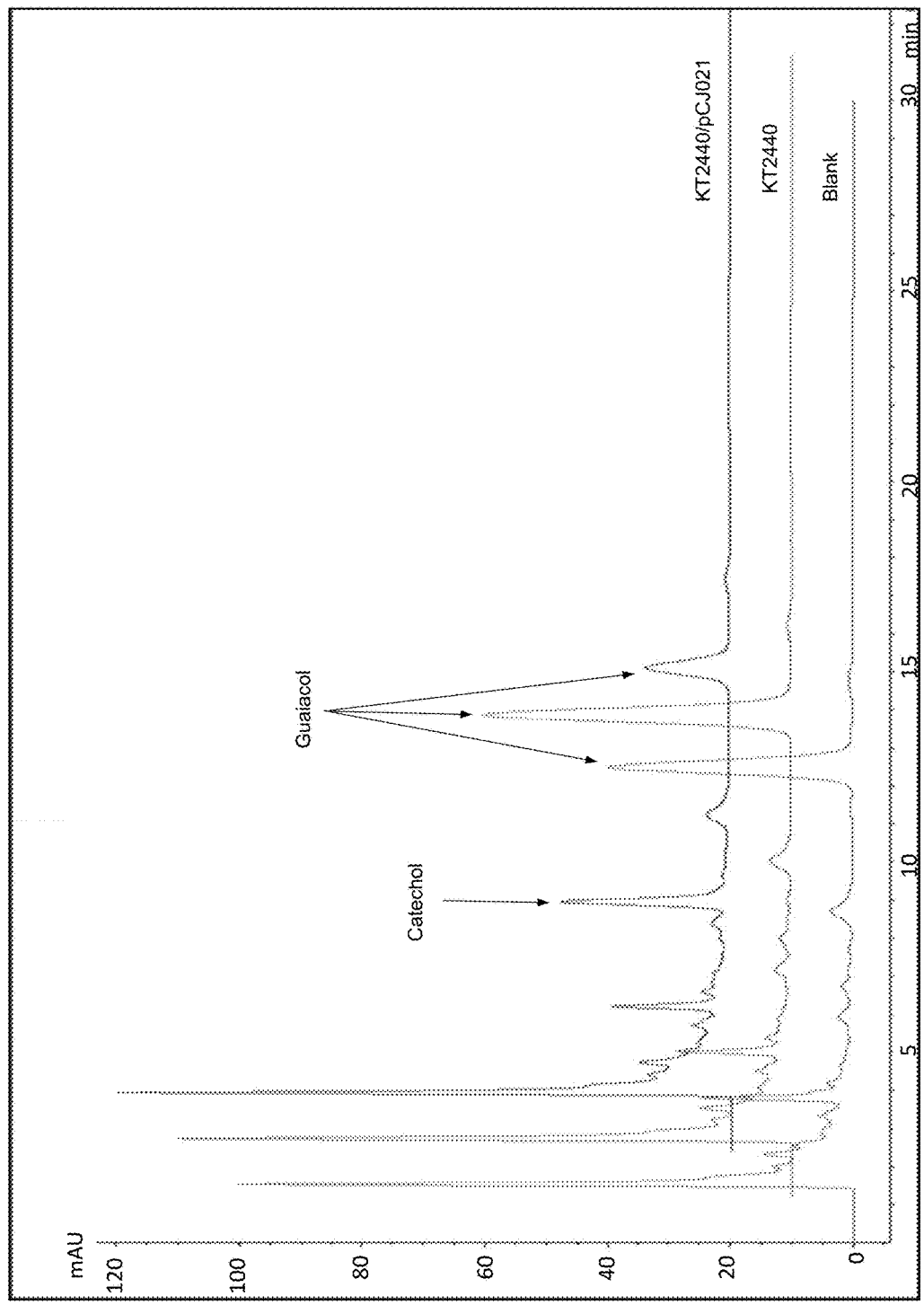
FIG. 5 shows guaiacol and catechol levels for *P. putida* KT2440 and *P. putida* KT2440/pCJ021 after growth on media containing guaiacol.
Figure 6:
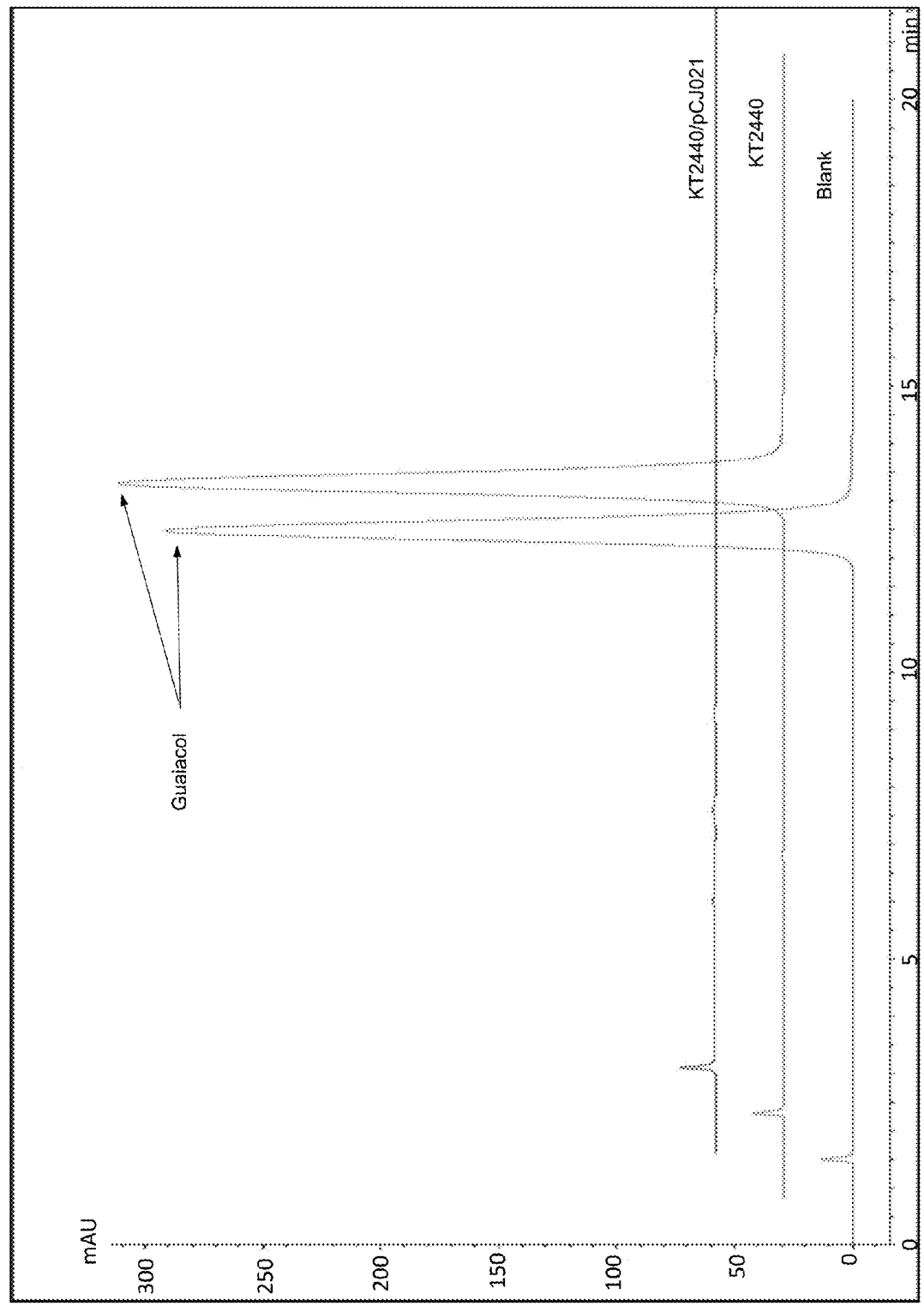
FIG. 6 shows guaiacol levels for *P. putida* KT2440 and *P. putida* KT2440/pCJ021 after growth on media containing guaiacol.

HPLC analyses show the disappearance of guaiacol in a culture of *P. putida* KT2440/pCJ021 grown on M9 minimal medium containing guaiacol and the lack of guaiacol catabolism by native *P. putida* KT2440 (FIG. 6). When these strains are grown in LB medium containing guaiacol, HPLC analysis shows the conversion of guaiacol to catechol (an increase in catechol levels and a corresponding decrease in guaiacol levels), which temporarily accumulated during catabolism of guaiacol (FIG. 5). These results indicate that the amplified genes encode a two-component cytochrome P450 system with guaiacol O-demethylase activity.

Conversion of anisole was demonstrated by growing *P. putida* KT2440/pCJ021 in LB medium containing anisole.

Figure 7:
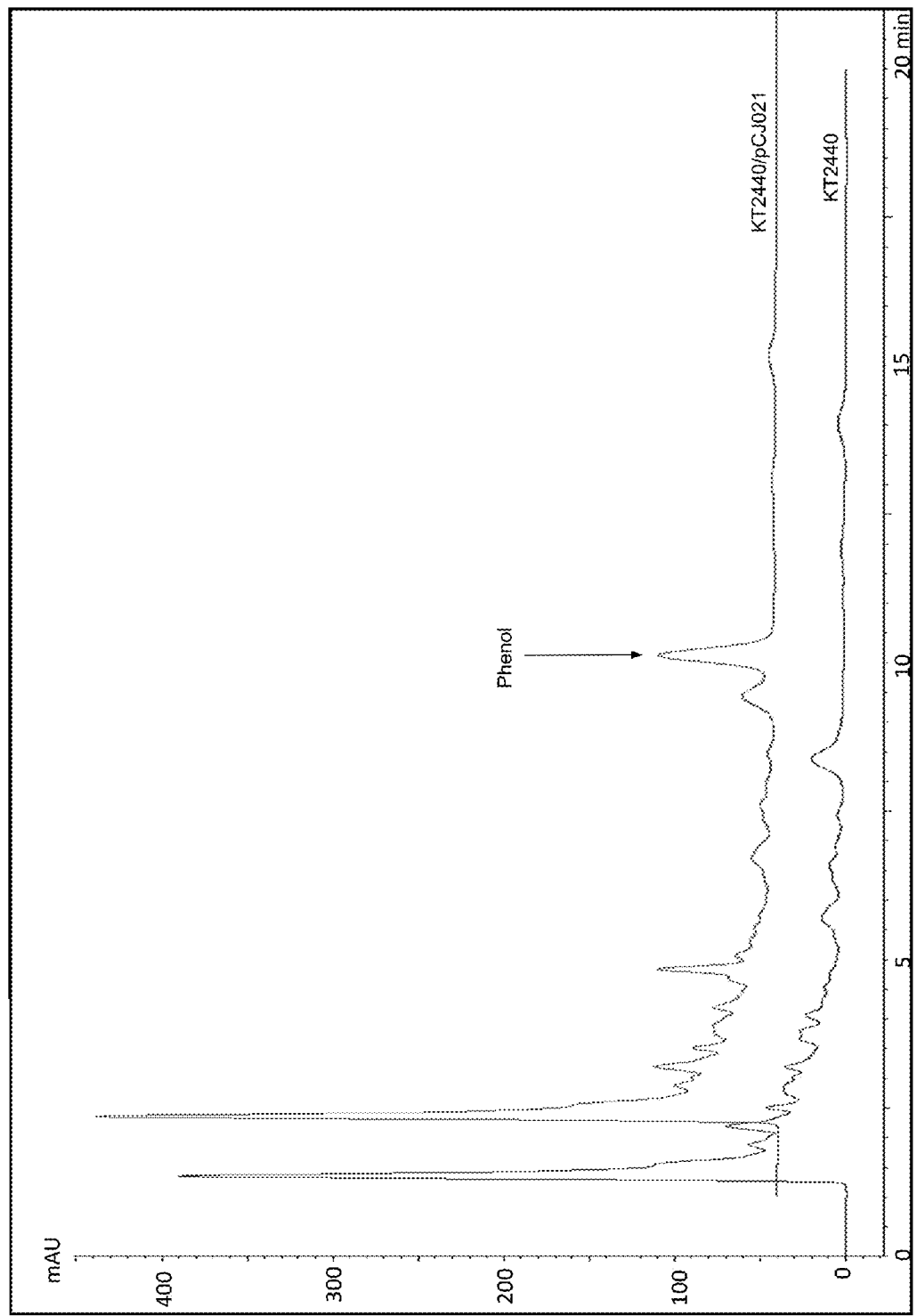
FIG. 7 shows phenol levels for *P. putida* KT2440 and *P. putida* KT2440/pCJ021 after growth on media containing anisole.

The cultures were grown in LB, a rich medium, because *P. putida* KT2440 cannot metabolize phenol. HPLC analysis of cultures of *P. putida* KT2440/pCJ021 grown in LB medium containing anisole demonstrated this strain catalyzed the conversion of anisole to phenol, which accumulates because *P. putida* KT2440 cannot metabolize it further. Control cultures of *P. putida* KT2440 did not accumulate phenol (FIG. 7). A peak corresponding to anisole was not observed due to the HPLC column used. The production of phenol, however, demonstrates that anisole is being demethylated to generate phenol in *P. putida* KT2440/pCJ021 cultures.

Figure 8:
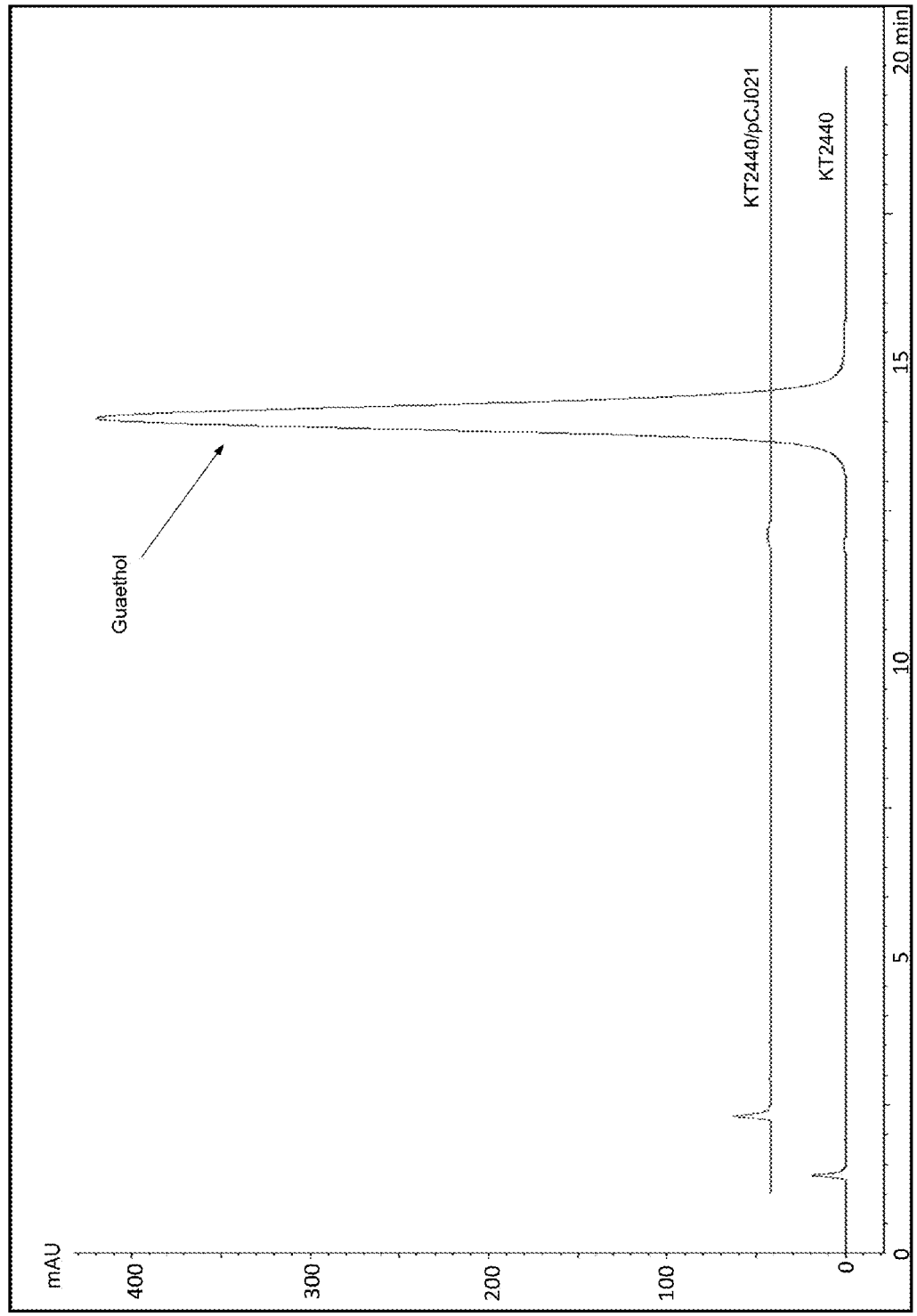
FIG. 8 shows guaethol levels for *P. putida* KT2440 and *P. putida* KT2440/pCJ021 after growth on media containing guaethol.
Figure 9:
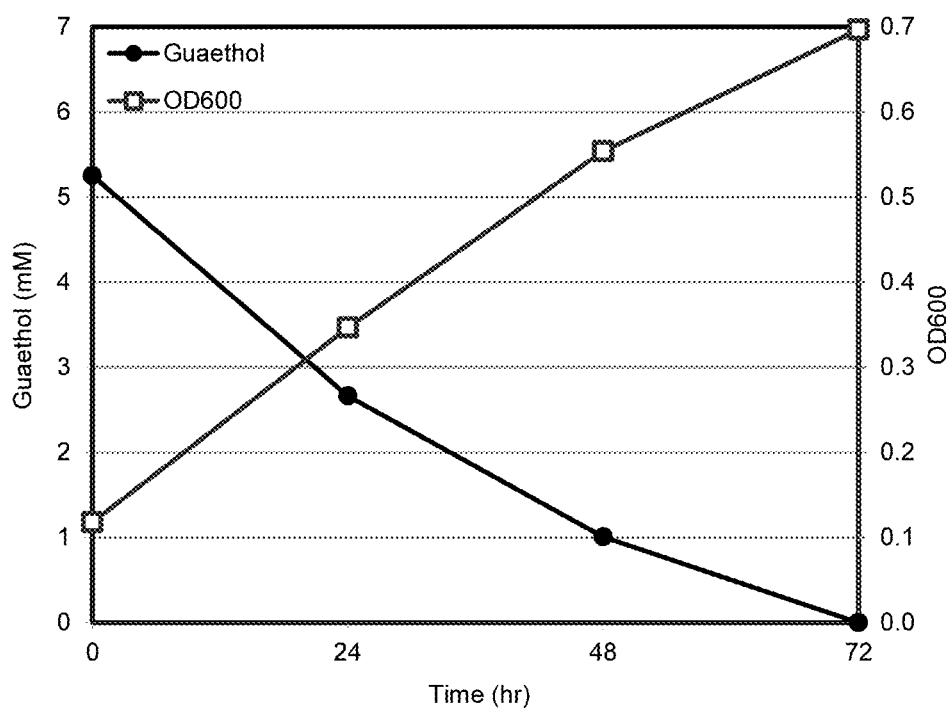
FIG. 9 shows growth of *P. putida* KT2440 engineered to express a cytochrome P450 O-dealkylase and a reductase (*P. putida* KT2440/pCJ021) on media containing guaethol.

Dealkylation of guaethol was demonstrated by growing *P. putida* KT2440/pCJ021 in M9 minimal medium containing 5 mM guaethol (2-ethoxyphenol). After 72 hours of growth with guaethol as the sole source of carbon and energy, *P. putida* KT2440/pCJ021 was able to metabolize the guaethol in the culture while native *P. putida* KT2440 was unable to metabolize guaethol. HPLC analysis shows the disappearance of guaethol in a culture of *P. putida* KT2440/pCJ021 after 72 hours, but not in a culture of native *P. putida* KT2440 (FIG. 8). *P. putida* KT2440/pCJ021 was able to grow to an $OD_{600}$ of 7 on the catechol produced in this reaction, as demonstrated in FIG. 9.

Taken together, these data demonstrate that the two-component cytochrome P450 system catalyzes the O-demethylation of guaiacol (2-methoxyphenol) to catechol (1,2-dihydroxybenzene), the O-demethylation of anisole (methoxybenzene) to phenol, and the O-deethylation of guaethol (2-ethoxyphenol) to catechol (FIG. 1).

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An isolated polynucleotide comprising a nucleic acid encoding a first polypeptide, a nucleic acid encoding a second polypeptide, and a promoter that is heterologous to the nucleic acid encoding said first or second polypeptide;
   wherein the promoter is operably linked to the nucleic acid encoding the first or second polypeptide,
   the first polypeptide has dealkylase activity and comprises the amino acid sequence of SEQ ID NO: 2, and
   the second polypeptide has reductase activity and comprises an amino acid sequence that has at least 99% sequence identity to the amino acid sequence of SEQ ID NO: 4.

2. An expression vector comprising the polynucleotide of claim 1.

3. An isolated host cell comprising the polynucleotide of claim 1.

4. The host cell of claim 3, wherein the host cell is a strain of *Pseudomonas*.

5. The isolated polynucleotide of claim 1, wherein the heterologous promoter is the lac promoter from *Escherichia coli*.

6. The host cell of claim 4, wherein the host cell is capable of growth on guaiacol and/or guaethol as a sole carbon source.

7. The host cell of claim 4, wherein the host cell is *P. putida*.

* * * * *